(12) United States Patent
Nagahama

(10) Patent No.: US 12,257,367 B2
(45) Date of Patent: Mar. 25, 2025

(54) BIOMATERIALS FOR BIOLOGICAL TISSUE REPAIR

(71) Applicant: KONAN GAKUEN, Kobe (JP)

(72) Inventor: Koji Nagahama, Kobe (JP)

(73) Assignee: KONAN GAKUEN, Kobe (JP)

( * ) Notice: Subject to any disclaimer, the term of this patent is extended or adjusted under 35 U.S.C. 154(b) by 515 days.

(21) Appl. No.: 16/939,204

(22) Filed: Jul. 27, 2020

(65) Prior Publication Data

US 2020/0405914 A1 Dec. 31, 2020

(30) Foreign Application Priority Data

May 27, 2019 (JP) ................. 2019-098693

(51) Int. Cl.
  *A61L 27/52* (2006.01)
  *A61L 27/20* (2006.01)
  *A61L 27/38* (2006.01)

(52) U.S. Cl.
  CPC ............... *A61L 27/52* (2013.01); *A61L 27/20* (2013.01); *A61L 27/3804* (2013.01); *A61L 27/3826* (2013.01); *A61L 27/3873* (2013.01)

(58) Field of Classification Search
  None
  See application file for complete search history.

(56) References Cited

U.S. PATENT DOCUMENTS

2010/0081240 A1   4/2010   Yagishita

FOREIGN PATENT DOCUMENTS

| JP | 2005-106533 A | 4/2005 |
| JP | 2006-138656 A | 6/2006 |
| JP | 2007-244374 A | 9/2007 |
| JP | 2015-40276 A | 3/2015 |

OTHER PUBLICATIONS

Blondiaux et al, J Tissue Eng Regen Med, 2017, 11: 3417-3427. (Year: 2017).*
Joo et al, Korean Circulation Journal, 2017, 47(2):151-159. (Year: 2017).*
Roche et al, Biomaterials, 2014, vol. 35, pp. 6850-6858. (Year: 2014).*
Hocking et al, Exp Cell Res, 2010, vol. 316, Issue 14, 15, pp. 22312-2219. (Year: 2010).*
International Search Report issued Sep. 24, 2020, in PCT/JP2020/028625.
Kimura and Nagahama, "Creation of cell cross-linked hydrogels and their function," Abstracts for the 17th Congress of the Japanese Society for Regenerative Medicine, P-01-113, p. 349, Mar. 21, 2018.
Nagahama et al., "Development of Smart Hydrogel for Cell Transport," Chemical Engineering (2019), vol. 64, No. 1, pp. 17-26.
Nagahama et al., "Fabrication of hydrogels in which cells are cross-linked with polymers and emergence of functions in the hydrogel using cellular reactions," Polymer Preprints, vol. 66, No. 2, The 66th Symposium on Macromolecules, 2017, 2 pages.
Nagahama et al., "Fabrication of hydrogels in which cells are cross-linked with polymers and emergence of functions in the hydrogel using cellular reactions," The 27th Symposium on Biopolymers, 2017, pp. 121-122.
Nagahama et al., "Preparation of neural cell cross-linked hydrogels and construction of neural network in the gels," Abstracts for the 17th Congress of the Japanese Society or Regenerative Medicine, P-01-080, p. 316, Mar. 21, 2018.
Nagahama, Koji, "Creation of smart gels with cell-crosslinking points and the development of functions using cellular reactions in gels", Report of results, Kaken, 2017, website: https://kaken.nii.ac.jp/report/KAKENHI-PROJECT-15K13791/15K137912017jisseki/2018.
Ueda, N. and K. Nagahama, "Development of technology for gelation of adipose stem cells and regeneration of skeletal muscle by topical administration of gel," The 19th Congress of The Japanese Society for Regenerative Medicine, P-02-15, 2020, 1 page.
Written Opinion of the International Searching Authority issued Sep. 24, 2020, in PCT/JP2020/028625.
Aoyama et al., "F3 Fabrication of neural cell cross-linked gels for regenerative medicine and evaluation of neural network formation conditions," Preprints, The 64th Annual Kobe Polymer Research Symposium, (Jul. 13, 2018), p. 97.
Aoyama S., and K. Nagahama, "P23 Fabrication of neural cell cross-linked hydrogels for regenerative medicine an evaluation of neural network formation conditions," Abstracts, The 28th Symposium on Biopolymers (Jul. 20, 2018), pp. 77-78.
Aoyama, S. and K. Nagahama, "2P-052 Development of hydrogels generated by cross-linking cells with polymers and effect of cell types on physical properties and functions of the hydrogels," Preprints; The 40th Annual Meeting of the Japanese Society for Biomaterials, on website (http://kokuhoken.haru.gs/jsbm/abstract/jsb_meet_40/page_all.pdf), Nov. 5, 2018, p. 423.
Aoyama, S. and K. Nagahama, "Development of cell gel blocks and three-dimensional molding of accumulated gel blocks," Poster Presentation, The 18th Congress of The Japanese Society for Regenerative Medicine (Mar. 23, 2019), 1 page.

(Continued)

*Primary Examiner* — Allison M Fox
(74) *Attorney, Agent, or Firm* — Birch, Stewart, Kolasch & Birch, LLP

(57) ABSTRACT

The present provides a biomaterial for repairing biological tissues, the biomaterial comprising: a water-soluble polymer having a reactive functional group A; and a cell having tissue-regenerating capacity and having, on the surface thereof, a reactive functional group B that can covalently bind to the reactive functional group A, wherein the biomaterial presents a hydrogel state when the reactive functional group A covalently binds to the reactive functional group B. Thus, the present invention can provide a biomaterial for repairing biological tissues that can exert excellent effect in repairing biological tissues by utilizing a hydrogel encapsulating cells having tissue-regenerating capacity.

16 Claims, 16 Drawing Sheets

(56) References Cited

OTHER PUBLICATIONS

Aoyama, S. and K. Nagahama, "Development of functional gells cross-linked with polymers and elucidation of effect of cell type on their physical properties and functions," Poster Presentation, The 40th Annual Meeting of the Japanese Society for Biomaterials (Nov. 13, 2018), 1 page.
Aoyama, S. and K. Nagahama, "Fabrication of hydrogels in which neural cells are cross-linked with polymers and analysis of their physical properties and cellular responses," Poster Presentation, The 67th session (2018) Symposium on Macromolecules (Sep. 13, 2018), 1 page.
Aoyama, S. and K. Nagahama, "Fabrication of neural cell cross-linked hydrogels for regenerative medicine and evaluation of neural network formation condition," Oral Presentation, The 64th Annual Kobe Polymer Research Symposium (Jul. 13, 2018), 13 pages.
Aoyama, S. and K. Nagahama, "Fabrication of neural cell cross-linked hydrogels for regenerative medicine and evaluation of neural network formation conditions," Poster Presentation, The 28th Symposium on Biopolymers (Jul. 26, 2018) 1 page.
Aoyama, S. and K. Nagahama, 2Pc051 Fabrication of hydrogels in which neural cells are cross-linked with polymers and analysis of their physical properties and cellular responses, Preprints (67(2)), The 67th session (2018) Symposium on Macromolecules (Aug. 29, 2018), 4 pages.
Aoyama, S., and K. Nagahama, "Poster 71/Tissue engineering (Cell organization 3)," Abstracts, The 18th Congress of The Japanese Society for Regenerative Medicine, on website (https://www.meeting-schedule.com/18jsrm/index.html), Feb. 22, 2019, P-03-110.
Kimura et al., "F2 Tissue regeneration using injectable cell cross-linked hydrogels," Preprints, The 64th Annual Kobe Polymer Research Symposium (Jul. 13, 2018), p. 96.
Kimura et al., "Fabrication of materials utilizing "cells" and "cell reactions," considering cells as living high-performance chemical materials," Oral Presentation, The 64th Annual Kobe Polymer Research Symposium (Jul. 13, 2018), 18 pages.
Kimura et al., "Fabrication of materials utilizing "cells" and "cellular reactions," considering cells as advanced living chemical materials," Oral Presentation, The 40th Annual Meeting of the Japanese Society for Biomaterials (Nov. 12, 2018), 22 pages.
Kimura et al., "P.3 Tissue regeneration using injectable cell cross-linked hydrogels," Abstracts, The 28th Symposium on Biopolymers (Jul. 20, 2018), pp. 37-38.
Kimura et al., "Tissue Engineering (Cell/Tissue) I/II 1C-07," Preprints, The 40th Annual Meeting of the Japanese Society for Biomaterials, on website (http://kokuhoken.haru.gs/jsbm/abstract/jsb_meet_40/page_all.pdf), Nov. 5, 2018, p. 104.
Kimura et al., "Tissue Regeneration using injectable cell cross-linked hydrogels," Poster Presentation, The 28th Symposium on Biopolymers (Jul. 26, 2018) 1 page.
Kimura, O, and K. Nagahama, "Regeneration of skeletal muscle using injectable cell cross-linked hydrogels," Poster Presentation, The 18th Congress of The Japanese Society for Regenerative Medicine (Mar. 23, 2019), 1 page.
Kimura, Y. and K. Nagahama, "1S13 Regeneration of skeletal muscles using injectable cell cross-linked gels," Preprints (67(2)), The 67th session (2018) Symposium on Macromolecules (Aug. 29, 2018), 4 pages.
Kimura, Y. and K. Nagahama, "Fabrication of materials utilizing "cells" and "cellular reactions," considering cells as advanced living chemical materials," Oral Presentation (in The 67th session (2018) Symposium on Macromolecules (Sep. 12, 2018), 22 pages.
Kimura, Y. and K. Nagahama, "Poster 66/Locomotorium (Biomaterial 2)," Abstracts, The 18th Congress of The Japanese Society for Regenerative Medicine, on website (https://www.meeting-schedule.com/18jsrm/index.html), Feb. 22, 2019, P-03-081.
Miyata et al., "Tumor marker-responsive behavior of gels prepared by biomolecular imprinting," PNAS (Jan. 31, 2006), vol. 103, No. 5, pp. 1190-1193.
Murakami, Y. and M. Maeda, "Hybrid Hydrogels to Which Single-Stranded (ss) DNA Probe is Incorporated Can Recognize Specific ssDNA," Macromolecules (2005), vol. 38, pp. 1535-1537.
Nagahama et al., "Biodegradable polymers exhibiting temperature-responsive sol-gel transition as injectable biomedical materials," Reactive and Functional Polymers (2013), vol. 73, pp. 979-985.
Nagahama et al., "Living Functional Hydrogels Generated by Bioorthogonal Cross-Linking Reactions of Azide-Modified Cells with Alkyne-Modified Polymers," Abstracts, 12th International Symposium on Nanomedicine (ISNM2018); Japan Nanomedicine Society (Dec. 6, 2018), p. 47.
Nagahama et al., "Living functional hydrogels generated by bioorthogonal cross-linking reactions of azide-modified cells with alkyne-modified polymers," Nature Communications (Jun. 6, 2018), vol. 9, No. 2195, 11 pages.
Nagahama et al., "Living functional hydrogels generated by bioorthogonal cross-linking reactions of azide-modified cells with alkyne-modified polymers," Oral Presentation, 12th International Symposium on Nanomedicine (Dec. 6, 2018), 19 pages.
Nagahama, K. and A. Takemoto, "Fabrication of hydrogels in which cells are cross-linked with polymers and emergence of functions in the hydrogel using cellular reactions," Oral Presentation, The 28th Symposium on Biopolymers (Jul. 20, 2017), 17 pages.
Nagahama, K. and A. Takemoto, "Fabrication of hydrogels in which cells are cross-linked with polymers and emergence of functions in the hydrogel using cellular reactions," Oral Presentation, The 66th session (2017) Symposium on Macromolecules (Sep. 6, 2017), 19 pages.
Nagahama, K. and S. Aoyama, "Preparation of neuroblast cross-linked hydrogels and construction of neural network in the gels;" Poster Presentation, The 17th Congress of The Japanese Society for Regenerative Medicine (Mar. 21, 2019), 1 page.
Dunn et al., "Biomaterial and Stem Cell-Based Strategies for Skeletal Muscle Regeneration," J. Orthop. Res. (2019), vol. 37, pp. 1246-1262.
Hamam, G. G., "Effect of Allogenic Bone Marrow-Versus Adiopse Tissue Derived Mesenchymal Stem Cells in Treatment of Experimental Skeletal Muscle Injury in Adult Femals Albino Rats: A Comparative Study," Journal of Stem Cell Biology and Transplantation (2019), vol. 3, No. 1:3, pp. 1-8.
Office Action issued Sep. 26, 2023, in Japanese Patent Application No. 2019-098693.
Qazi et al., "Biomaterials based strategies for skeletal muscle tissue engineering: Existing technologies and future trends," Biomaterials (2015), vol. 53, pp. 502-521.

* cited by examiner

[Fig. 1]
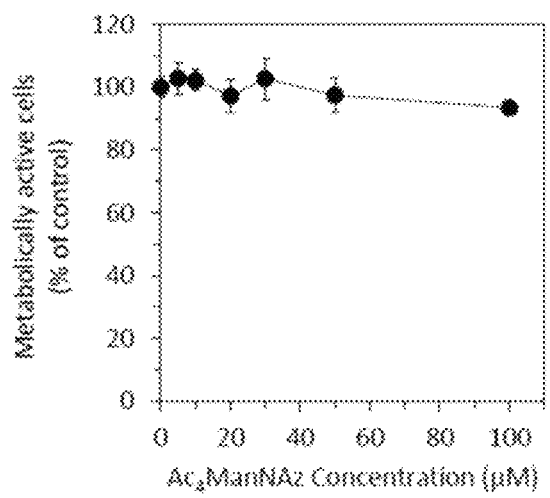
[Fig. 2]
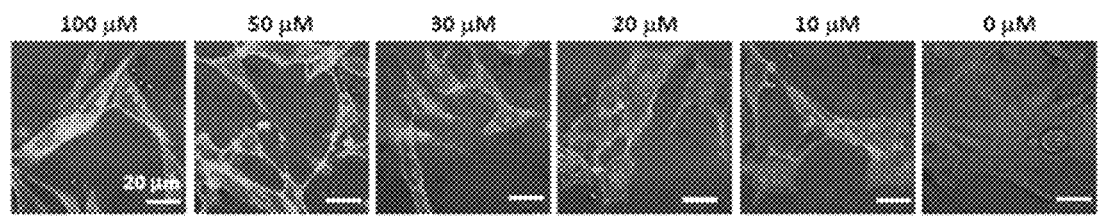
[Fig. 3]
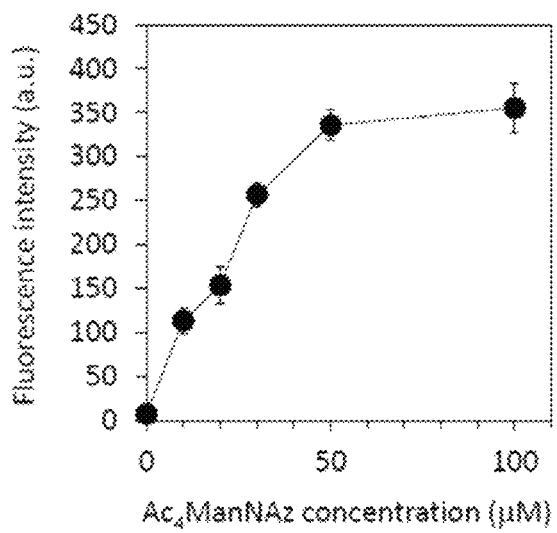

[Fig. 4]
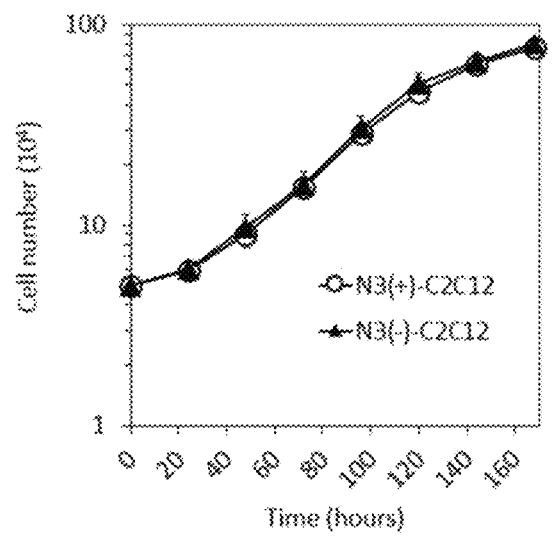
[Fig. 5]
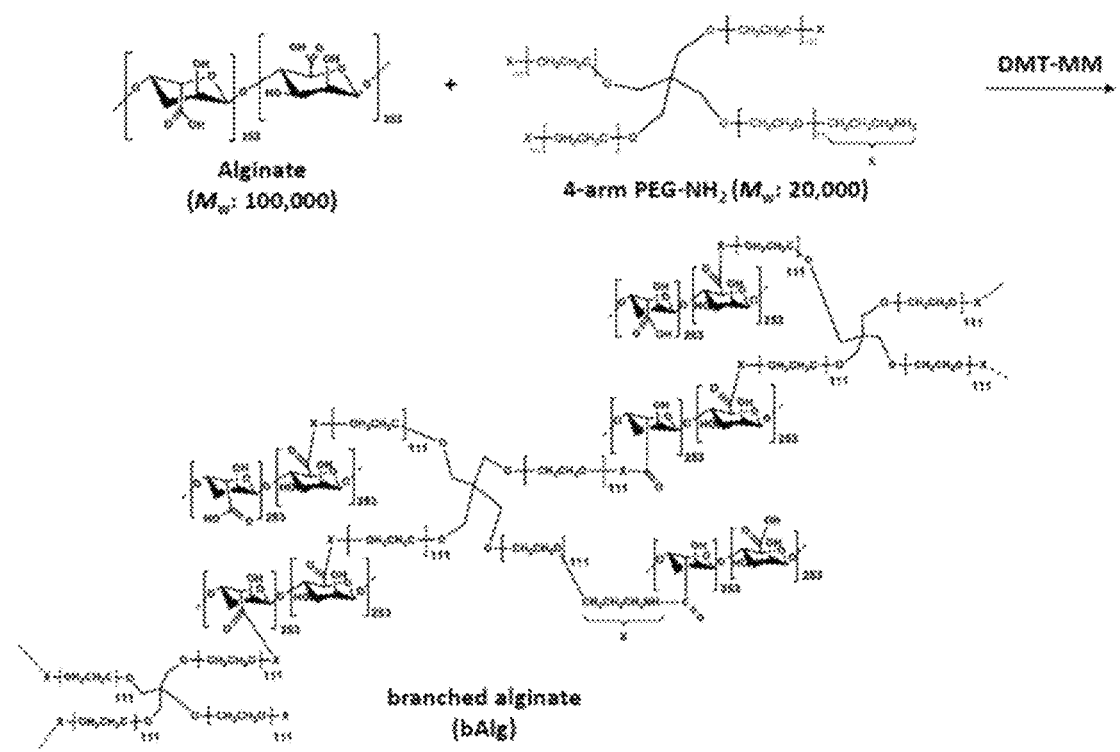

[Fig. 6]
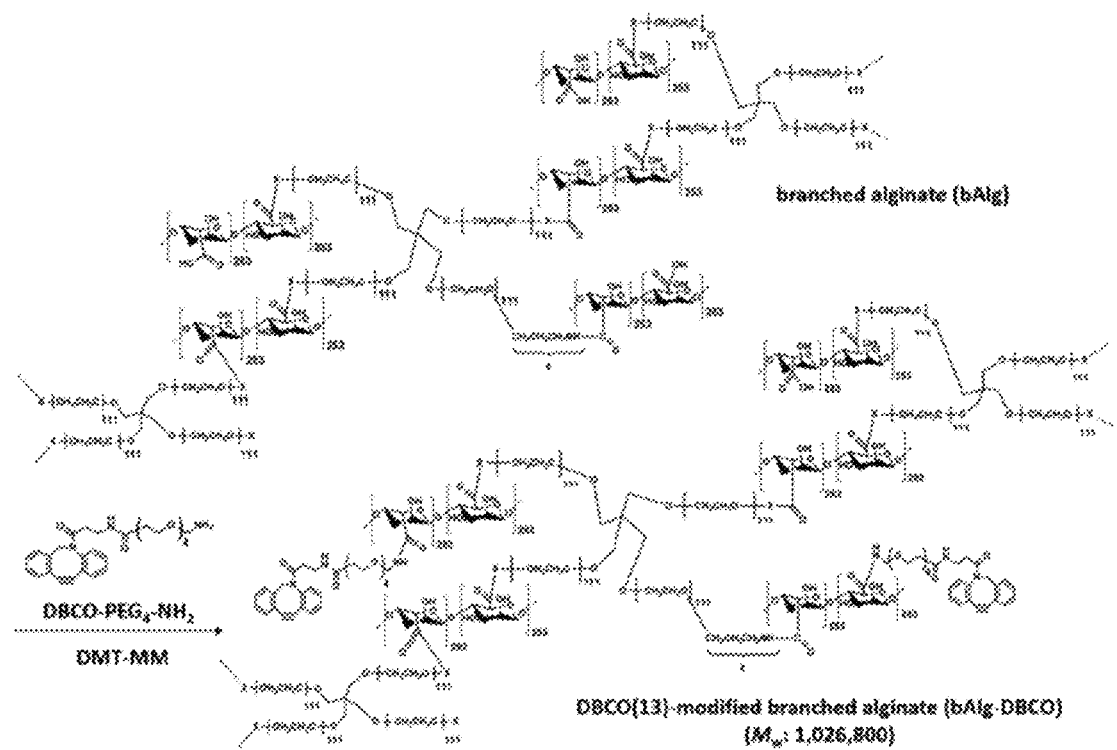
[Fig. 7]
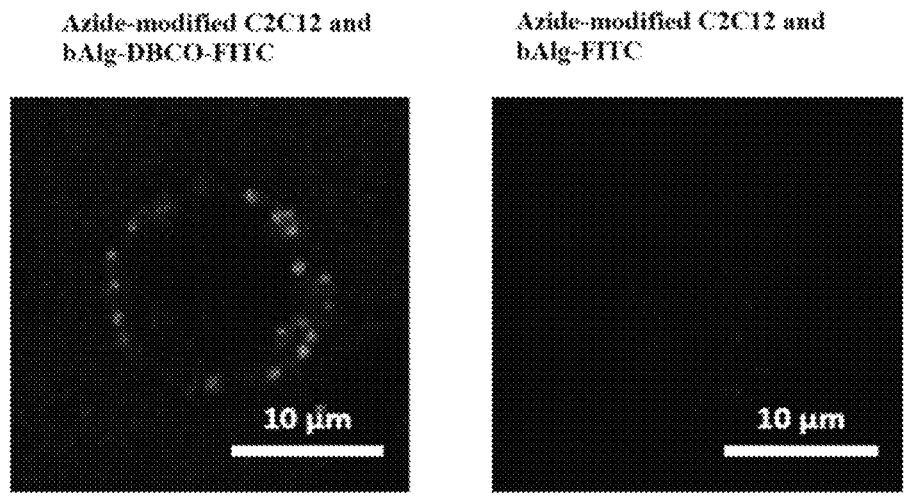

[Fig. 8]
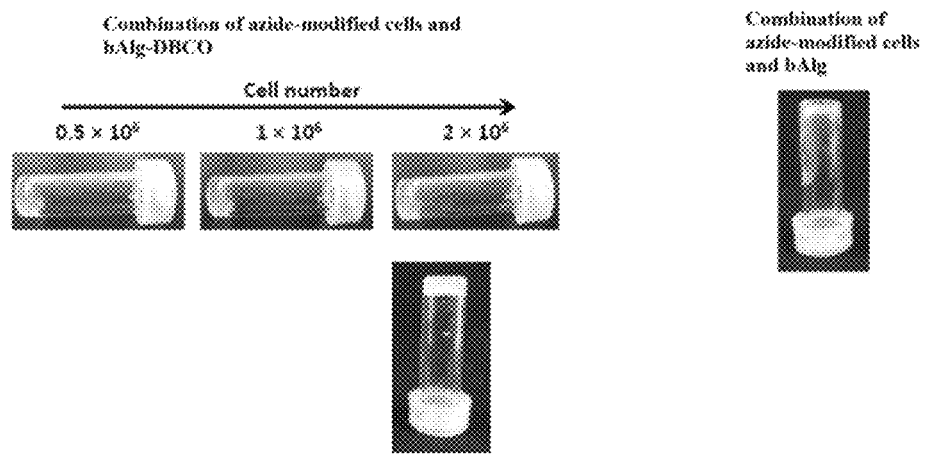
[Fig. 9]
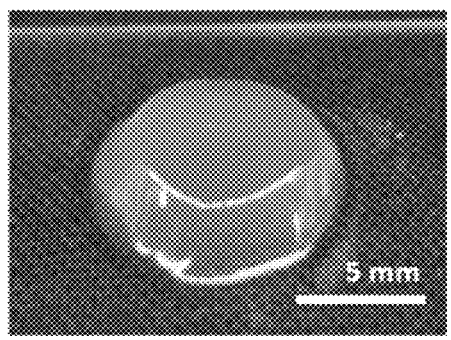
[Fig. 10]
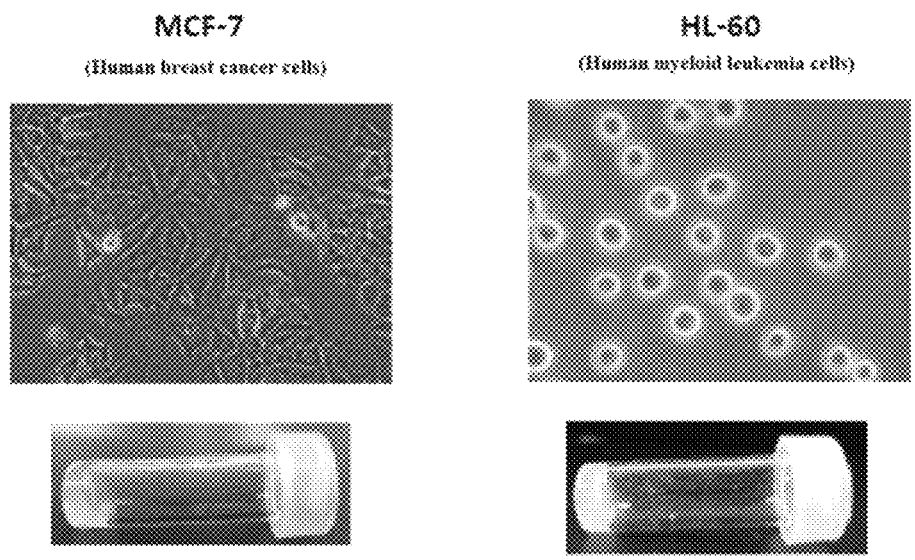

[Fig. 11]
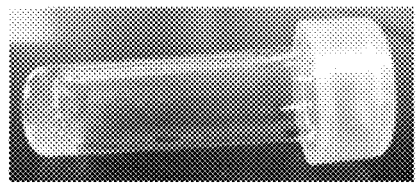
[Fig. 12]
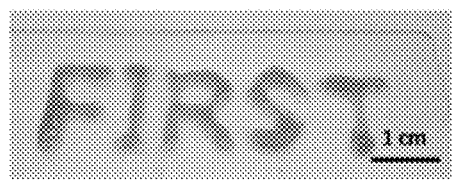
[Fig. 13]
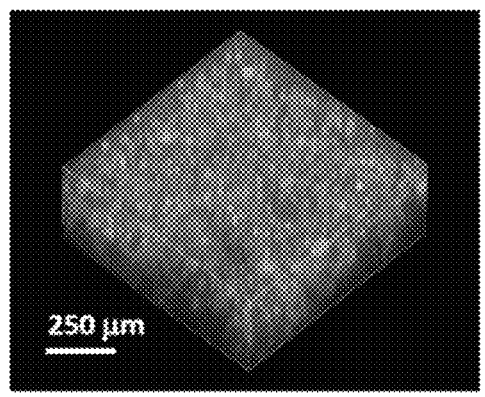
[Fig. 14]
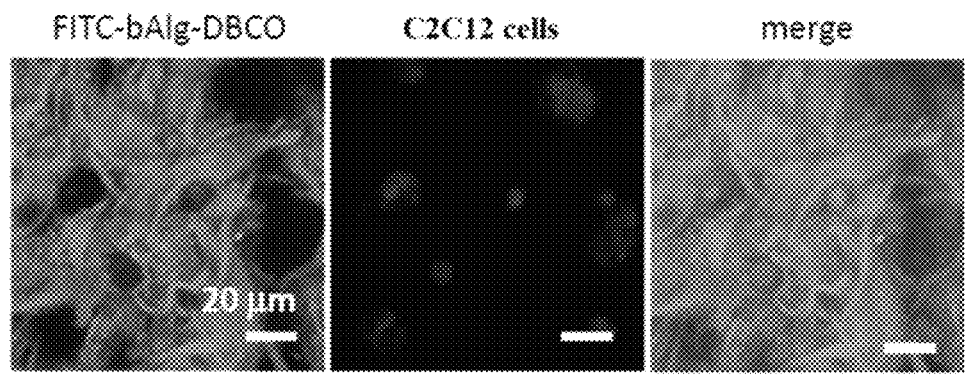

[Fig. 15]
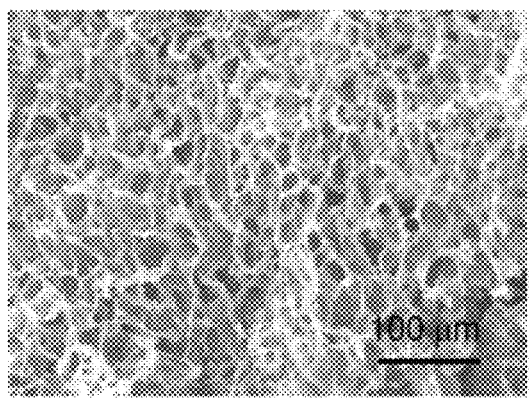
[Fig. 16]
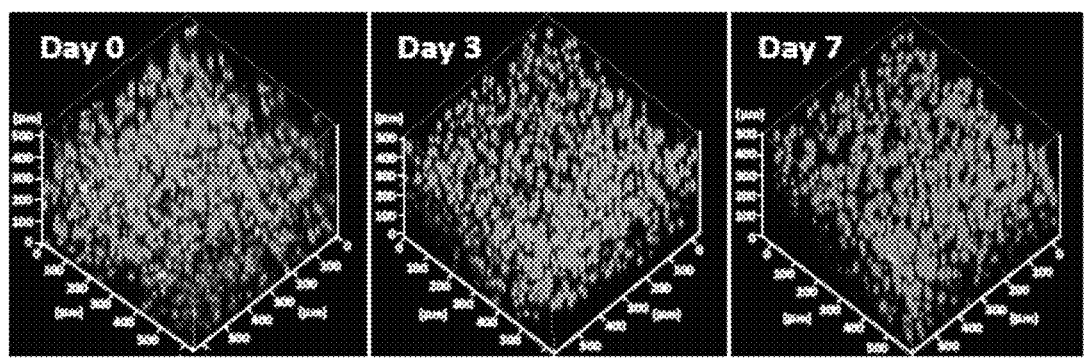

[Fig. 17]
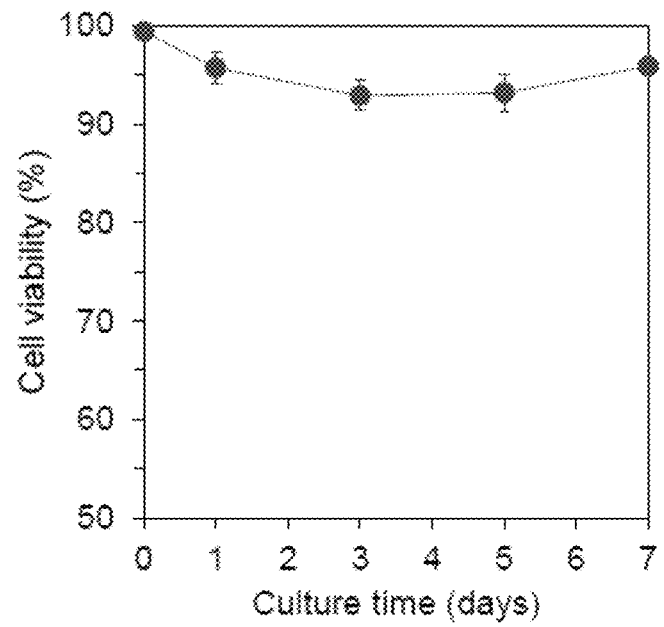
[Fig. 18]
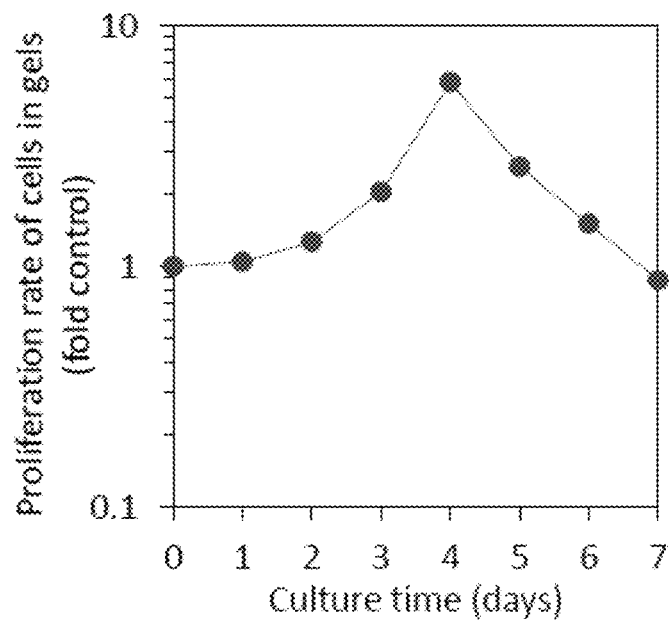

[Fig. 19]
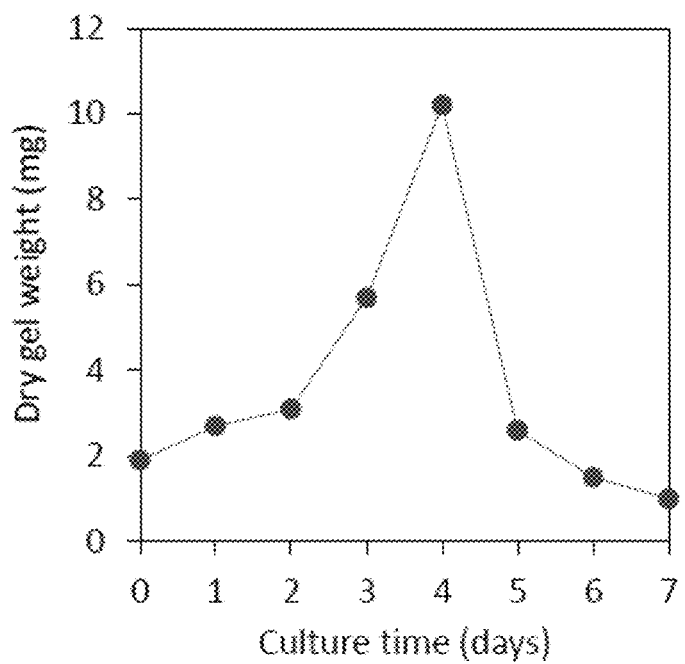

[Fig. 20]
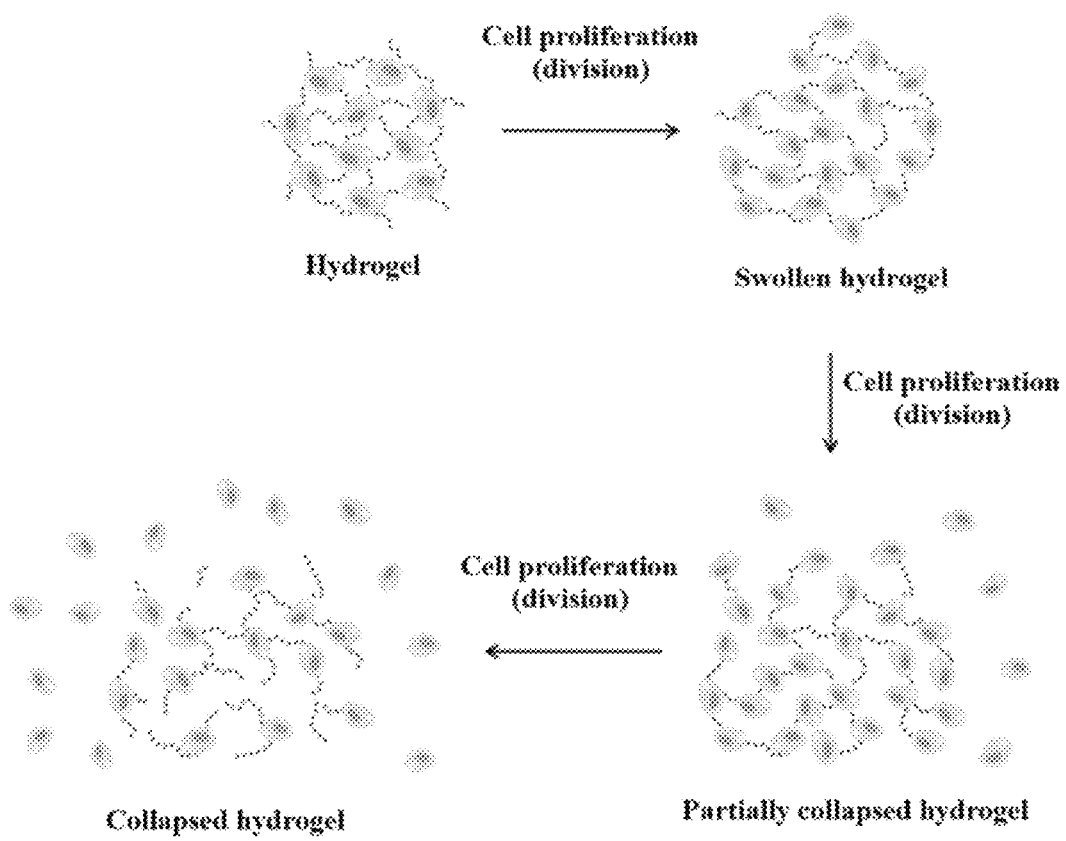

[Fig. 21]
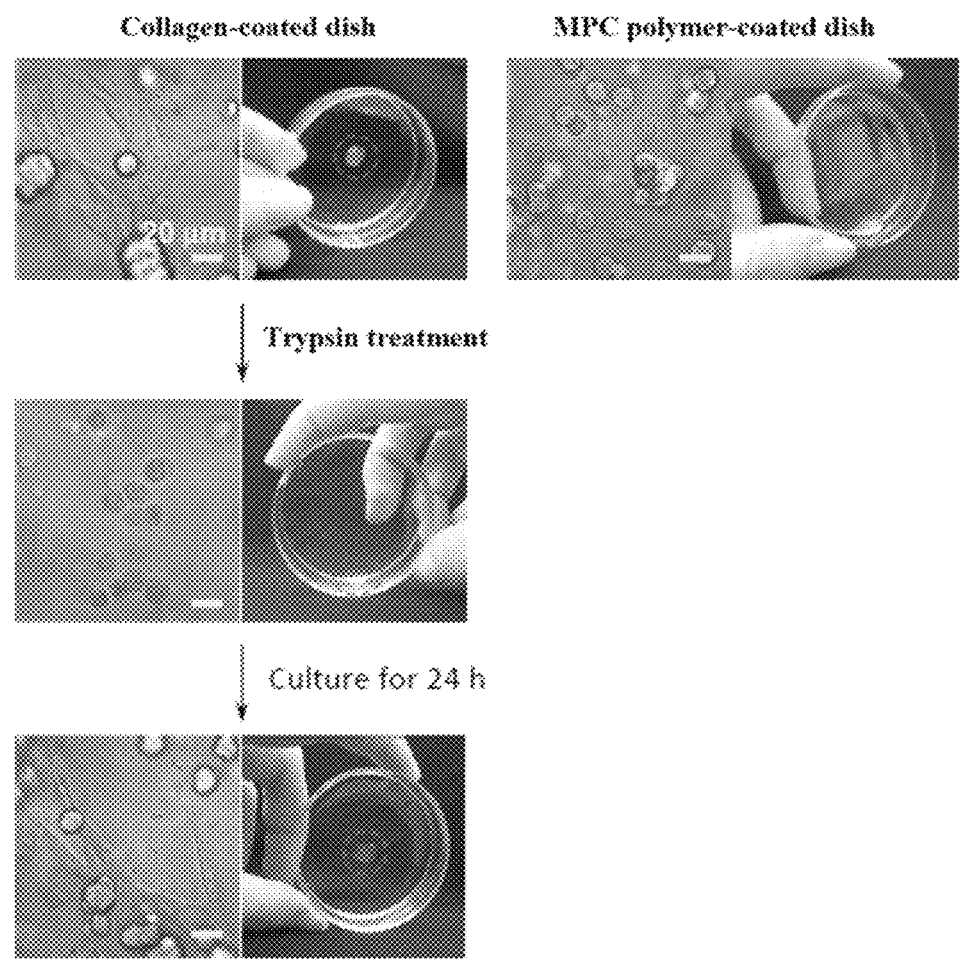

[Fig. 22]
Before overlaying hydrogel     After overlaying hydrogel
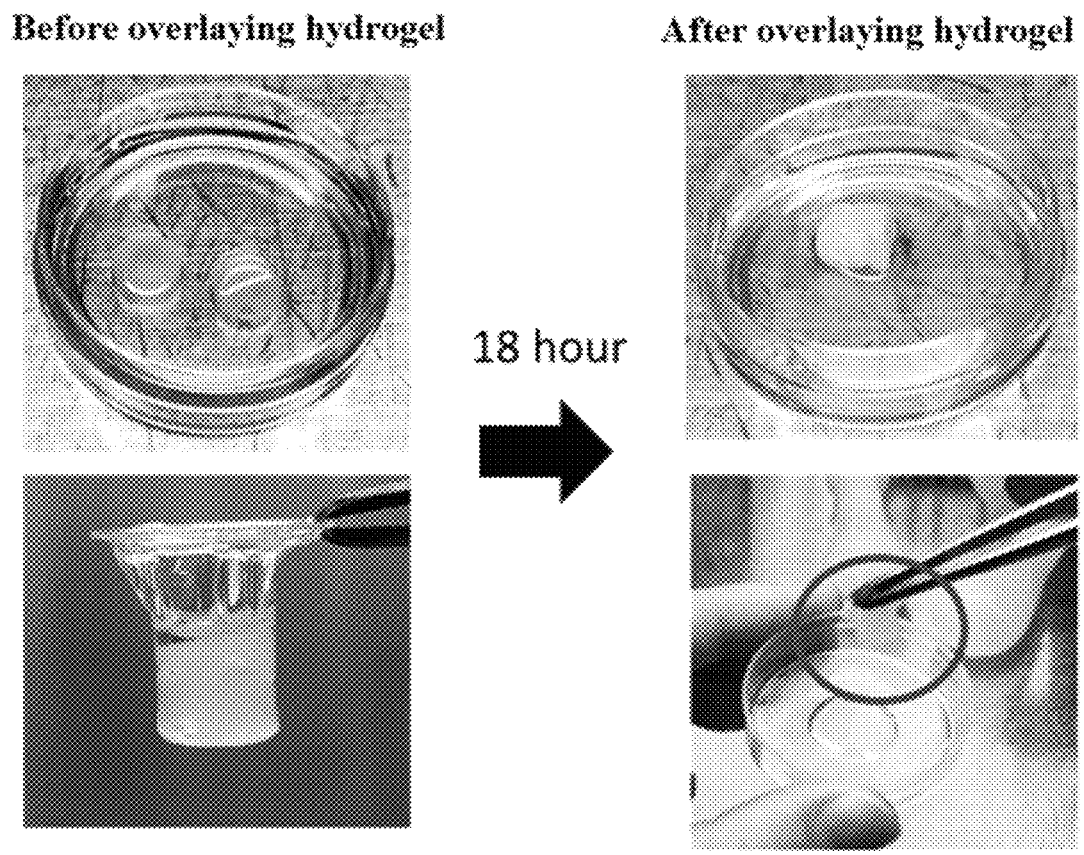
18 hour
[Fig. 23]
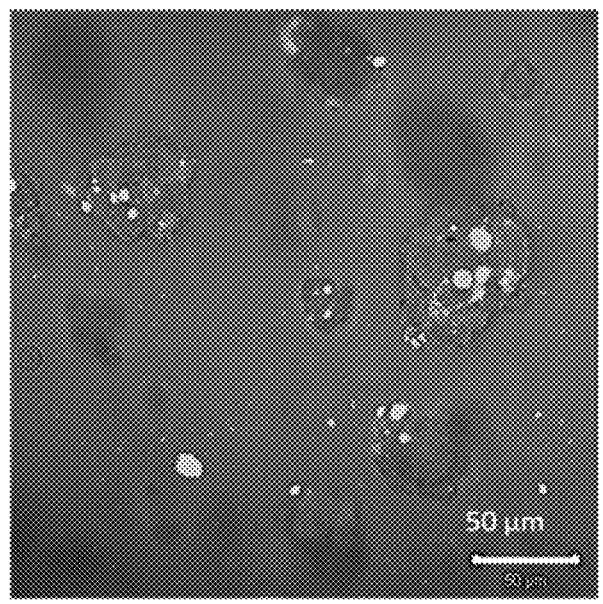

[Fig. 24]
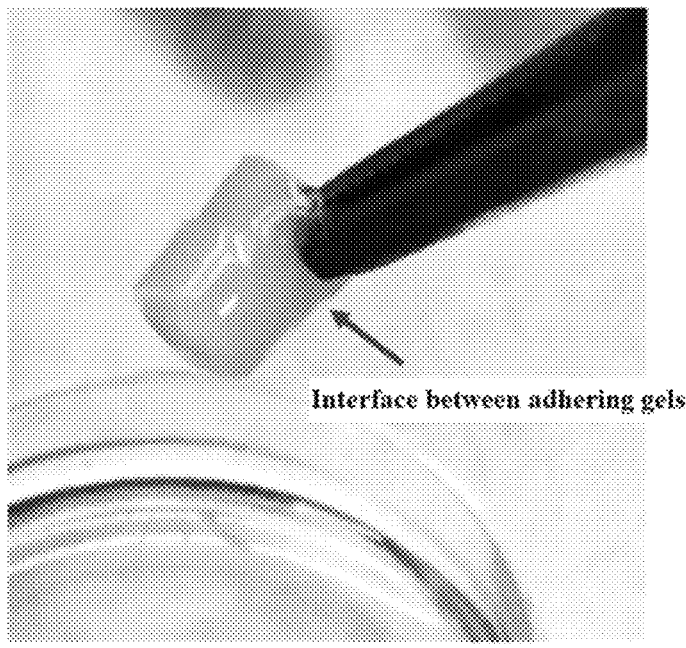
[Fig. 25]
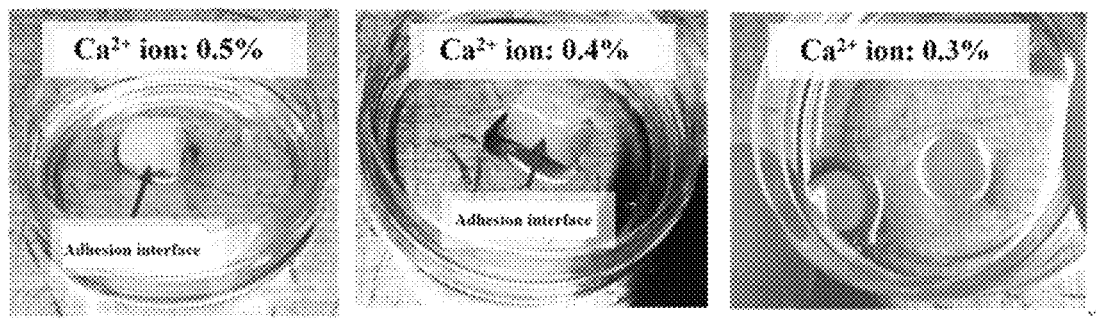

[Fig. 26]
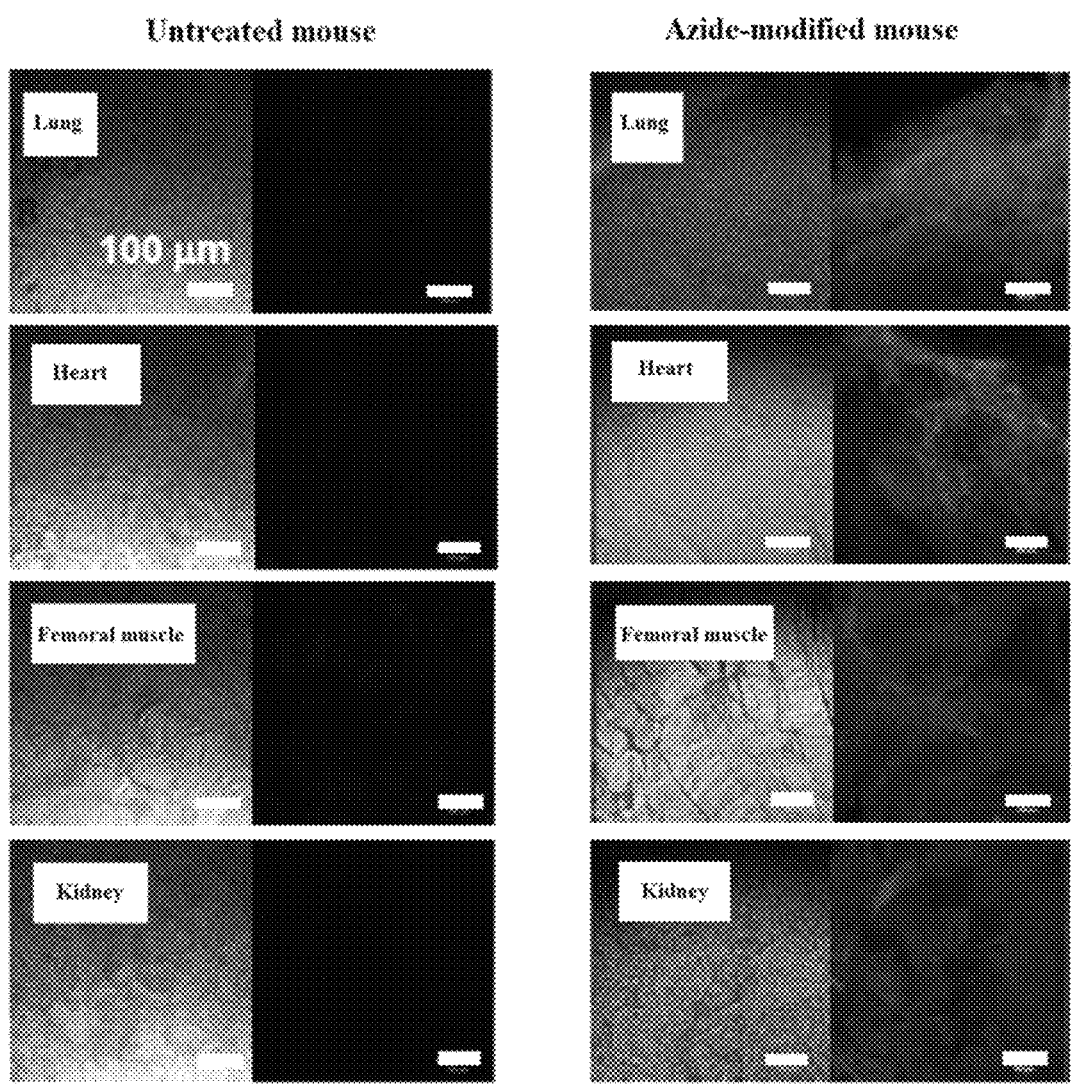

[Fig. 27]
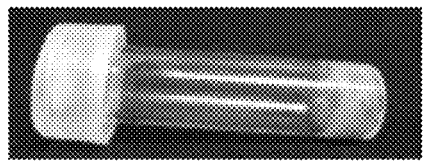
Lung
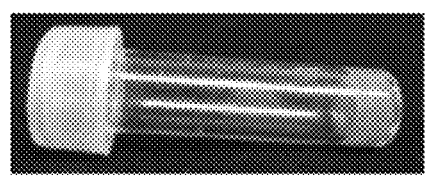
Heart
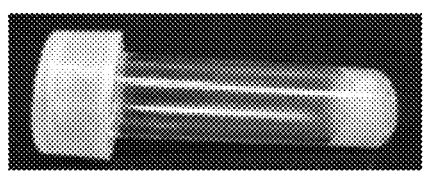
Femoral muscle
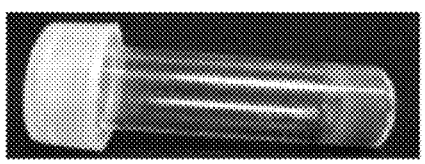
Kidney
[Fig. 28]
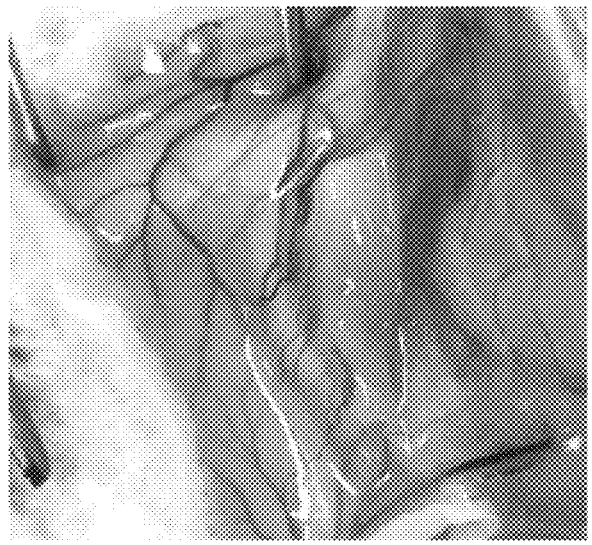

[Fig. 29]
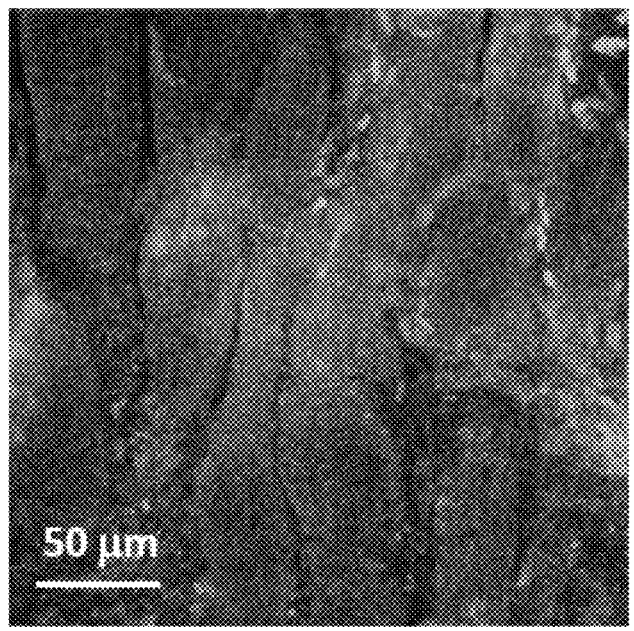
[Fig. 30]
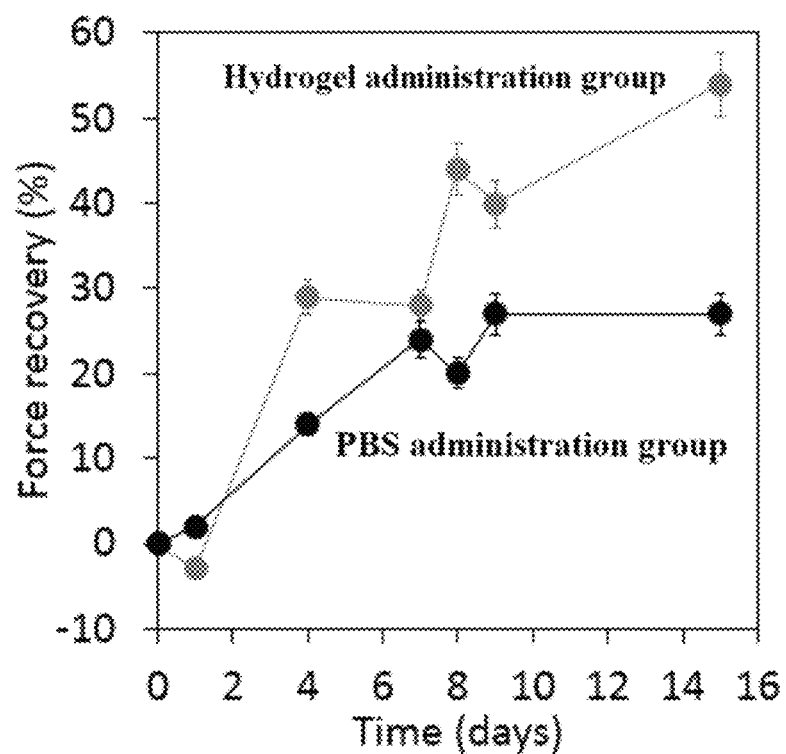

[Fig. 31]
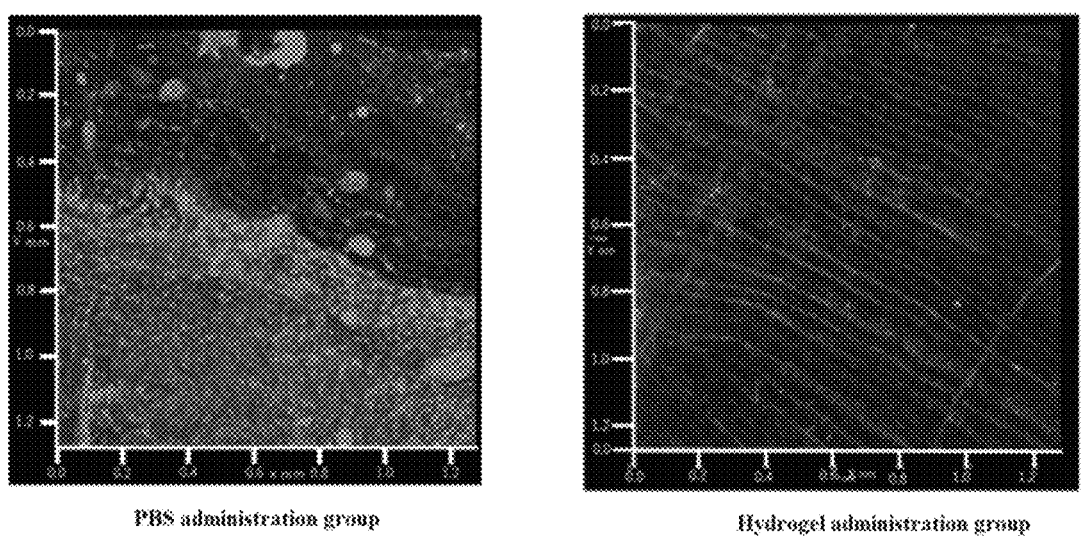
[Fig. 32]
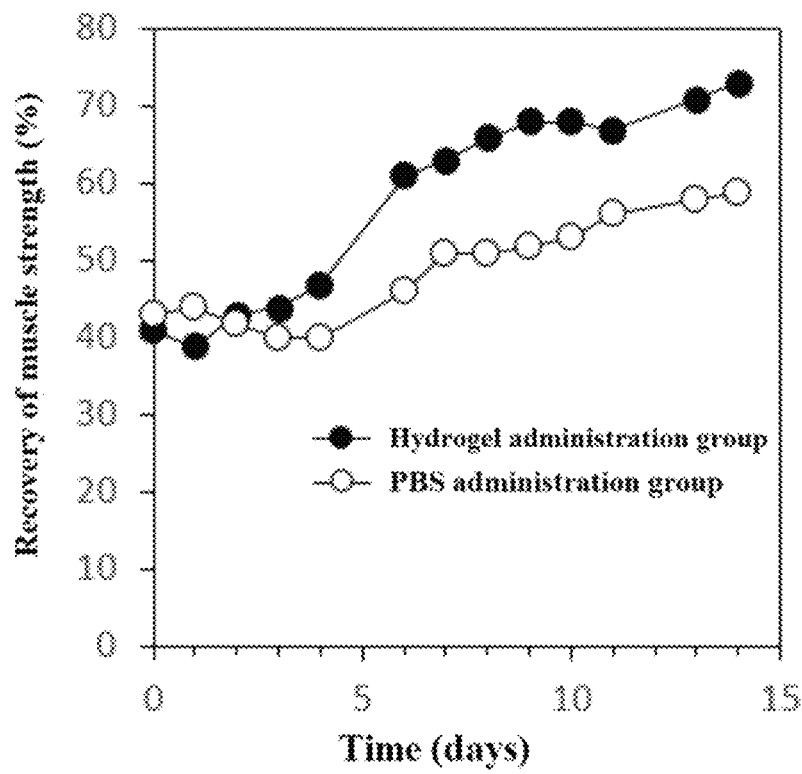

BIOMATERIALS FOR BIOLOGICAL TISSUE REPAIR

FIELD OF THE INVENTION

The present invention relates to a biomaterial for repairing biological tissues, which uses cells having tissue-regenerating capacity as cross-linking points so that a water-soluble polymer is cross-linked to present a gel state, thereby exerting excellent effect in repairing biological tissues.

BACKGROUND ART

A hydrogel is a soft material made of a three-dimensional network of polymers swollen in water. Since it has properties like a water-absorbing property, a substance-loading property, a substance-releasing property, a substance-separating property and the like, it is widely used in food products, cosmetics, daily necessities, environmental fields and the like. Furthermore, since hydrogel has unique properties such as flexibility, elasticity, biocompatibility and a cell loading property, it is expected for application and expansion to medical-related fields that require high performance, specifically, sensors, diagnostic devices, drug delivery systems, regenerative medicine and the like.

Lately, for the purpose of developing a hydrogel applicable to medical-related fields, gels in which highly functional biomolecules (substance) such as nucleic acids and proteins (including peptides) are covalently hybridized with a polymer network have been developed. These biomolecular hybrid gels are reported to have excellent characteristics that cannot be achieved with conventional polymer gels. For example, in a case of a nucleic acid hybrid gel, once single-stranded nucleic acids immobilized on a polymer network recognize nucleic acids of a completely complementary nucleotide sequence, they form double strands, by which the gel shrinks. Therefore, the presence of a nucleic acid molecule having a specific nucleotide sequence can be detected by shrinkage of the gel (see Patent document 1 and Non-patent document 1). Alternatively, in a case of a gel in which double-stranded nucleic acids are immobilized on a polymer network, the double strands are dissociated once either one of the strands recognizes, if any, completely complementary nucleotide acids, by which the gel swells. Therefore, the presence of a nucleic acid molecule having a specific nucleotide sequence can be detected by swelling of the gel. Moreover, since such a gel shows different swelling behaviors between completely complementary nucleic acids and single-base mismatched nucleic acids, it can be used to identify a single base difference (see Patent document 2). Moreover, as to protein hybrid gels, gels in which an antibody is immobilized on a polymer network have been developed (see Patent document 3 and Non-patent document 2). Since such a protein hybrid gel forms an antigen-antibody complex and shrinks if any specific antigen is present, the presence or absence of an antigen can be detected by shrinkage of the gel. Since biomolecular hybrid gels can detect the presence of a target molecule via their macro-response (swelling and shrinkage), they are expected for application to sensors and diagnostic devices.

In addition, techniques utilizing cells having tissue-regenerating capacity for repairing injured tissues have been gaining attention, and various composite materials encapsulating cells in gels have been studied. For example, a composite material, in which cells are encapsulated in a hydrogel containing a water-soluble, biodegradable, temperature-responsive polymer and a clay mineral having a nanosheet structure, is reported to be effective in repairing an injured tissue (Patent document 4). The conventional composite materials encapsulating cells in the gels, however, may not exert a sufficient effect for regenerating tissues since the cells are physically loaded in the gel and thus the cells and growth factors produced by the cells may be released outside the gel upon administration to an injured tissue. Thus, there have been demands for further improvement.

PRIOR ART DOCUMENTS

Non-Patent Documents

Non-patent document 1: Y. Murakami, M. Maeda, Macromolecules, 38, 1535-1537 (2005)

Non-patent document 2: T. Miyata, M. Jige, T. Nakaminami, T. Uragami, Proc. Natl. Acad. Sci. USA, 103, 1190 (2006)

Patent Documents

Patent document 1: Japanese Unexamined Patent Application Publication No. 2005-106533

Patent document 2: Japanese Unexamined Patent Application Publication No. 2007-244374

Patent document 3: Japanese Unexamined Patent Application Publication No. 2006-138656

Patent document 4: Japanese Unexamined Patent Application Publication No. 2015-40276

SUMMARY OF INVENTION

Problem to be Solved by Invention

The objective of the present invention is to provide a biomaterial for repairing biological tissues, which exerts an excellent effect for regenerating biological tissues by utilizing a hydrogel encapsulating cells having tissue-regenerating capacity.

Means for Solving Problem

Thus, the present invention provides an invention in the following aspects.

Item 1. A biomaterial for repairing a biological tissue, comprising:

a water-soluble polymer having a reactive functional group A; and a cell having tissue-regenerating capacity and having, on the surface thereof, a reactive functional group B that can covalently bind to the reactive functional group A, wherein the biomaterial presents a hydrogel state when the reactive functional group A covalently binds to the reactive functional group B.

Item 2. The biomaterial for repairing a biological tissue according to Item 1, wherein the reactive functional group A is an alkynyl group and the reactive functional group B is an azide group.

Item 3. The biomaterial for repairing a biological tissue according to Item 1 or 2, wherein the water-soluble polymer is a polysaccharide thickener.

Item 4. The biomaterial for repairing a biological tissue according to Item 3, wherein the polysaccharide thickener is alginate.

Item 5. The biomaterial for repairing a biological tissue according to any one of Items 1-4, wherein the water-soluble polymer is branched as two or more linear water-soluble polymers are bound to a branched compound.

Item 6. The biomaterial for repairing a biological tissue according to Item 2, wherein the biomaterial is in a gel state or a sol state prior to administration, and the reactive functional group A covalently binds to the reactive functional group B at the affected site and thus the biomaterial presents a hydrogel state after administration.

Item 7. The biomaterial for repairing a biological tissue according to any one of Items 1-5, which is applicable to an injured or defect muscle tissue.

BRIEF DESCRIPTION OF THE DRAWINGS

FIG. 1 A chart showing results from WST-1 assay for analyzing cytotoxicity of azide-modified mannosamine ($Ac_4ManNAz$).

FIG. 2 Images results obtained by allowing carboxyrhodamine 110 DBCO to react with C2C12 cells cultured in a DMEM medium containing $Ac_4ManNAz$ to observe with a confocal microscope.

FIG. 3 A chart showing results obtained by allowing carboxyrhodamine 110 DBCO to react with C2C12 cells cultured in DMEM media containing $Ac_4ManNAz$ to quantify the fluorescence intensities on the surfaces of the cell membranes.

FIG. 4 A chart showing cell growth curves of azide-modified C2C12 cells and non-azide-modified C2C12 cells.

FIG. 5 A diagram showing a synthesis pathway of branched alginate (bAlg).

FIG. 6 A diagram showing a synthesis pathway of cyclooctyne-modified branched alginate (bAlg-DBCO).

FIG. 7 Images showing results obtained by observing azide-modified C2C12 cells reacted with bAlg-DBCO-FITC and azide-modified C2C12 cells reacted with bAlg-FITC with a confocal microscope.

FIG. 8 Pictures showing results obtained by mixing bAlg-DBCO or bAlg with azide-modified cells to confirm the presence of hydrogel formation by a test tube inverting method.

FIG. 9 A picture showing a result obtained by adding a DMEM medium to a hydrogel formed by combining $2 \times 10^6$ azide-modified cells and a 2% bAlg-DBCO solution, leaving the resultant to stand still for an hour, and removing the medium therefrom to observe the appearance of the hydrogel.

FIG. 10 Images showing results obtained by mixing bAlg-DBCO with azide-modified MCF-7 cells or azide-modified HL-60 cells to confirm the presence of gel formation by a test tube inverting method.

FIG. 11 A picture showing a result obtained by mixing cryopreserved azide-modified cells with bAlg-DBCO to confirm the presence of gel formation by a test tube inverting method.

FIG. 12 A picture showing a result obtained by mixing azide-modified cells with bAlg-DBCO and using the resultant to write the word "FIRST" on a glass slide, which was left to stand still in a $CO_2$ incubator at 37° C. for 30 minutes to thereafter observe the appearance thereof.

FIG. 13 An image showing a result obtained when a hydrogel fabricated using azide-modified C2C12 cells and bAlg-DBCO-FITC was observed with a confocal microscope.

FIG. 14 Images showing partially enlarged views inside the hydrogel fabricated using azide-modified C2C12 cells and bAlg-DBCO-FITC observed with a confocal microscope.

FIG. 15 A SEM image of a fractured surface of a lyophilized hydrogel fabricated using azide-modified C2C12 cells and bAlg-DBCO-FITC.

FIG. 16 Images showing results obtained by fabricating a hydrogel using azide-modified C2C12 cells and bAlg-DBCO, and staining the hydrogel with Calcein AM and PI solutions to observe it with a confocal microscope after predetermined days of culture following fabrication (Days 0, 3 and 7).

FIG. 17 A chart showing a result obtained by fabricating a hydrogel using azide-modified C2C12 cells and bAlg-DBCO, and determining the cell viability with time after fabrication.

FIG. 18 A chart showing a result obtained by fabricating a hydrogel using azide-modified C2C12 cells and bAlg-DBCO, and determining the number of azide-modified C2C12 cells in the hydrogel with time after fabrication.

FIG. 19 A chart showing a result obtained by fabricating a hydrogel using azide-modified C2C12 cells and bAlg-DBCO, and determining the dry weight of the hydrogel with time after fabrication.

FIG. 20 A diagram showing an assumed mechanism of degradation of the hydrogel of the present invention.

FIG. 21 Images showing results obtained by forming a hydrogel on a MPC polymer-coated dish and a collagen-coated dish by using azide-modified C2C12 cells and bAlg-DBCO, and evaluating adhesion of the hydrogel to respective dishes.

FIG. 22 Pictures showing results obtained by overlaying and leaving two hydrogels that were formed using azide-modified C2C12 cells and bAlg-DBCO to stand still to observe adhesion of the two hydrogels.

FIG. 23 An image showing results obtained by allowing alkyne-modified rhodamine to react with a hydrogel formed using azide-modified C2C12 cells and bAlg-DBCO and observing the resultant with a confocal microscope.

FIG. 24 A picture showing a result obtained by allowing alkyne-modified rhodamine to react with two hydrogels each formed using azide-modified C2C12 cells and bAlg-DBCO, overlaying and leaving the two hydrogels to stand still, and observing adhesion of the two hydrogels.

FIG. 25 Pictures showing results obtained by overlaying two hydrogels that were each formed using azide-modified C2C12 cells and bAlg-DBCO, leaving the resultant to stand still in DMEM media containing calcium ions (0.3 wt %, 0.4 wt % and 0.5 wt %), and thereafter observing adhesion of the two hydrogels.

FIG. 26 Images showing results obtained by allowing respective tissues (lung, cardiac muscle, skeletal muscle, kidney) resected from an untreated mouse and respective tissues resected from a mouse administered with a $Ac_4ManNAz$ solution to react with bAlg-DBCO-FITC to observe the resultants with a confocal microscope.

FIG. 27 Pictures showing results obtained by allowing respective tissues (lung, cardiac muscle, skeletal muscle, kidney) resected from the untreated mice and respective tissues resected from the mice administered with a $Ac_4ManNAz$ solution to react with bAlg-DBCO-FITC to observe the presence of formation of a hydrogel.

FIG. 28 A picture showing a result obtained by subcutaneously administering a suspension containing azide-modified C2C12 cells and bAlg-DBCO to a mouse, and incising the administered site 30 minutes after administration to observe said site.

FIG. 29 An image showing a result obtained by administrating a suspension containing azide-modified C2C12 cells and bAlg-DBCO to an injured site of a mouse whose inner femoral muscle of one limb was injured (hydrogel administration group), and observing the injured site with a fluorescence microscope 15 days after making the injury.

FIG. 30 A chart showing results obtained by administrating a suspension containing azide-modified C2C12 cells and bAlg-DBCO (hydrogel administration group) or PBS containing C2C12 cells (PBS administration group) to an injured site of a mouse whose inner femoral muscle of one limb was injured, and measuring the muscle strength of the injured limb with time.

FIG. 31 Images showing results obtained by administrating a suspension containing azide-modified ADSC and bAlg-DBCO (hydrogel administration group) or PBS containing ADSC (PBS administration group) to an injured site of a mouse whose inner femoral muscle of one limb was injured, and observing the injured site with a fluorescence microscope 14 days after making the injury.

FIG. 32 A chart showing results obtained by administrating a suspension containing azide-modified ADSC and bAlg-DBCO (hydrogel administration group) or PBS containing ADSC (PBS administration group) to an injured site of a mouse whose inner femoral muscle of one limb was injured, and measuring the muscle strength of the injured limb with time.

EFFECT OF THE INVENTION

Since cells having tissue-regenerating capacity are chemically bound to a water-soluble polymer in the hydrogel of the biomaterial of the present invention, the cells are retained in the hydrogel and remain at the affected site even after they are administered to an injured site, thereby effectively repairing the injured site.

In addition, while a biomaterial in one aspect of the present invention is in a gel state or a sol state upon administration, it can form a hydrogel at the affected site after administration and therefore cells can be transplanted in a form of an injectable gel.

MODE FOR CARRYING OUT THE INVENTION

The biomaterial of the present invention is a biomaterial used for the purpose of repairing biological tissues, which is characterized in that the biomaterial comprises: a water-soluble polymer having a reactive functional group A; and a cell having tissue-regenerating capacity and having, on the surface thereof, a reactive functional group B that can covalently bind to the reactive functional group A, and that the biomaterial presents a hydrogel state when the reactive functional group A covalently binds to the reactive functional group B. Hereinafter, the biomaterial of the present invention will be described in detail.

[Water-Soluble Polymer]

The biomaterial of the present invention uses a water-soluble polymer having a reactive functional group A as a scaffold for forming a hydrogel.

Any type of water-soluble polymer can be used as long as it is biocompatible and presents a hydrogel state upon covalently binding with cells serving as cross-linking points. Specifically, examples of the water-soluble polymer include polysaccharide thickeners such as alginate, chondroitin, pectin, gellan gum, carrageenan, curdlan, hyaluronic acid and agarose; proteins such as collagen, gelatin and fibrin; and synthetic macromolecules such as polyethylene glycol, MPC (2-methacryloyloxyethyl phosphorylcholine) polymer and block copolymers thereof. Among these water-soluble polymers, a polysaccharide thickener is preferable and alginate is more preferable.

Furthermore, in order to facilitate formation of a hydrogel, the water-soluble polymer is preferably linked with a branched compound having two or more (preferably 2-10) reactive functional groups bound to a linear water-soluble polymer (hereinafter, a branching agent) so as to be branched. While the type of the branching agent is not particularly limited as long as it can link with the water-soluble polymer for branching, preferable examples include multi-arm polyethylene glycol derivatives. While 2-arm, 3-arm, 4-arm and 8-arm polyethylene glycol derivatives and the like are known as multi-arm polyethylene glycol derivatives, a 4-arm polyethylene glycol derivative that can be used as a branching agent may be, for example, a compound having the structure represented by General formula (1) below.

[Chemical formula 1]

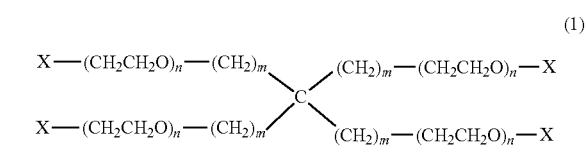

In General formula (1), m represents a number of the methylene groups, which is, for example, 1-10, preferably 1-5 and more preferably 1.

In General formula (1), n represents an average number of moles of ethylene oxide added, which is, for example, 10-500, preferably 10-300 and more preferably 10-200.

In General formula (1), X is a reactive functional group that can bind with a functional group of a linear water-soluble polymer to be bound. While X (reactive functional group) can suitably be determined according to the type of the functional group of the linear water-soluble polymer to be bound, it may suitably be selected from, for example, a carboxyl group, a N-succinimide group, a sulfhydryl group, a pyridyl sulfide group, a maleimide group, an amino group and the like. For example, when a linear water-soluble polymer to be bound has a carboxyl group, X (reactive functional group) may be an amino group. Alternatively, when a linear water-soluble polymer to be bound has an amino group, X (reactive functional group) may be selected from a carboxyl group and a N-succinimide group. When a linear water-soluble polymer to be bound has a sulfhydryl group, X (reactive functional group) may be selected from a sulfhydryl group, a pyridyl sulfide group and a maleimide group.

In order to bind a branching agent to a linear water-soluble polymer for branching, a known technique can be employed to bind a reactive functional group of the branching agent to a reactive functional group of the linear water-soluble polymer.

Moreover, when a branching agent is bound to obtain a branched water-soluble polymer, the ratio of the linear water-soluble polymer and the branching agent may suitably be determined according to the type and the molecular weight of the linear water-soluble polymer, the number of the reactive functional groups of the branching agent, and the like. The ratio is, for example, such that the number of molecules of the branching agent is 1-20, preferably 2-20 and more preferably 2-10 to 1 molecule of the linear water-soluble polymer constituting the branched water-soluble polymer.

The water-soluble polymer used in the present invention has a reactive functional group A that can covalently bind with a reactive functional group B of a cell having tissue-regenerating capacity so as to chemically bind with the cell having tissue-regenerating capacity to form a hydrogel.

While the type of the reactive functional group A may suitably be determined according to the type of the reactive functional group B of the cell having tissue-regenerating capacity, it may suitably be selected from, for example, an alkynyl group, an azide group, a carboxyl group, an amino group, a N-succinimide group, a sulfhydryl group, a pyridyl sulfide group, a maleimide group and the like. More specifically, if the reactive functional group B is an azide group, an alkynyl group may be selected as the reactive functional group A. If the reactive functional group B is an alkynyl group, an azide group may be selected as the reactive functional group A. Alternatively, if the reactive functional group B is a carboxyl group or a N-succinimide group, an amino group may be selected as the reactive functional group A. If the reactive functional group B is an amino group, the reactive functional group A may be selected from a carboxyl group and a N-succinimide group. If the reactive functional group B is a sulfhydryl group, the reactive functional group A may be selected from a sulfhydryl group, a pyridyl sulfide group and a maleimide group. If the reactive functional group B is a pyridyl sulfide group, a sulfhydryl group may be selected as the reactive functional group A. Alternatively, if the reactive functional group B is a maleimide group, a sulfhydryl group may be selected as the reactive functional group A.

Among these reactive functional groups A, an alkynyl group and an azide group are preferable since they are prone to chemical binding via click chemistry. Specifically, a combination of an alkynyl group as the reactive functional group A incorporated into the water-soluble polymer and an azide group as the reactive functional group B of the cell having tissue-regenerating capacity; or a combination of an azide group as the reactive functional group A incorporated into in the water-soluble polymer and an alkynyl group as the reactive functional group B of the cell having tissue-regenerating capacity, is preferable.

Moreover, while the number of the reactive functional groups A incorporated into the water-soluble polymer is not particularly limited, it is, for example, 2-60, preferably 5-50 and more preferably 5-30 per molecule of the water-soluble polymer.

In order to introduce a reactive functional group A into the water-soluble polymer, a bifunctional linker having a reactive functional group A and a reactive functional group C that can bind to the functional group of the water-soluble polymer may be used so as to bind the reactive functional group C to the functional group of the water-soluble polymer. While the reactive functional group C can suitably be determined according to the type of the functional group of the linear water-soluble polymer to be bound, it may suitably be selected from, for example, a carboxyl group, a N-succinimide group, a sulfhydryl group, a pyridyl sulfide group, a maleimide group, an amino group and the like. For example, if the water-soluble polymer has a carboxyl group, the reactive functional group C may be an amino group. Alternatively, if the water-soluble polymer has an amino group, the reactive functional group C may be selected from a carboxyl group and a N-succinimide group. If the water-soluble polymer has a sulfhydryl group, the reactive functional group C may be selected from, a sulfhydryl group, a pyridyl sulfide group and a maleimide group.

The bifunctional linker having the reactive functional group A and the reactive functional group C may be those that are known or those that can be synthesized by a known technique.

[Cell Having Tissue-Regenerating Capacity]

The biomaterial of the present invention uses a cell having tissue-regenerating capacity and having, on the surface thereof, a reactive functional group B that can covalently bind to the reactive functional group A. By using such a cell, the cell itself can serve as a cross-linking point of the water-soluble polymer, contributing to formation of a hydrogel. Furthermore, since the cell having tissue-regenerating capacity is retained in the hydrogel via chemical binding in the biomaterial of the present invention, it is maintained in the hydrogel without being released therefrom upon administration to an affected site, thereby effectively promoting tissue regeneration.

Any type of cell can be used in the biomaterial of the present invention as long as it has tissue-regenerating capacity and it can contribute to repairing of an injured tissue, and such a cell may suitably be selected according to the injured tissue targeted for administration. Examples of such a cell include myoblasts, osteoblasts, chondroblasts, mesenchymal stem cells, iPS cells, muscle satellite cells, cardiomyocytes and Muse cells.

The cell used in the present invention has a reactive functional group B that can covalently bind with a reactive functional group A of the above-described water-soluble polymer, which can serve as a cross-linking point of the hydrogel for chemically binding with the above-described water-soluble polymer.

While the type of the reactive functional group B can suitably be selected according to the type of the reactive functional group A of the above-described water-soluble polymer, it can be selected, for example, from an alkynyl group, an azide group, a carboxyl group, an amino group, a N-succinimide group, a sulfhydryl group, a pyridyl sulfide group, a maleimide group and the like.

As already described above, since an alkynyl group and an azide group are prone to chemical binding via click chemistry, the reactive functional group B is preferably an alkynyl group or an azide group.

In order to allow the reactive functional group B to exist on the cell surface, for example, the reactive functional group B may be introduced into sialic acid contained in the glycan present on the cell surface. Specifically, the reactive functional group B may be bound to a sugar that is metabolized into sialic acid (for example, mannosamine) and the cell may be cultured in a medium containing the sugar having the reactive functional group B, thereby obtaining a cell having sialic acid bound to the reactive functional group B on the cell surface.

More specifically, a bifunctional linker having a carboxyl group or a N-succinimide group and the reactive functional group B is used to bind the carboxyl group or the N-succinimide group of the bifunctional linker to an amino group of mannosamine to synthesize mannosamine having the reactive functional group B. Then, cells can be cultured in a medium containing said mannosamine having the reactive functional group B so that said mannosamine having the reactive functional group B receives sugar metabolism reaction of the cell to be converted into sialic acid having the reactive functional group B which can serve as a structural component of the glycan on the cell surface, thereby obtaining a cell having the reactive functional group B on the cell surface. Here, mannosamine having the reactive functional group B used for culturing the cell may be subjected to acetylation or the like so that no hydroxyl group exists. If no hydroxyl group moiety exists, the reactive functional group B can be linked with sialic acid at the end of the glycan on the cell surface, which facilitates a covalent bond with the water-soluble polymer. Moreover, while the concentration of mannosamine having the reactive functional group in the medium for culturing the cell can suitably be determined according to, for example, the amount of the reactive functional group B to be incorporated, it is, for example, 10-200 µM, preferably 10-100 µM and more preferably 40-100 µM. In addition, the time for culturing the cell using mannosamine having the reactive functional group B is, for example, 6-96 hours, preferably 12-72 hours and more preferably 24-72 hours.

[Hydrogel]

In the case of the biomaterial of the present invention, a water-soluble polymer having a reactive functional group A and a cell having, on the surface thereof, a functional group B that can covalently bind to the reactive functional group A are placed together in an environment containing water so that the reactive functional group A covalently binds to the reactive functional group B, thereby forming a hydrogel having the cell as a cross-linking point.

In the case of the biomaterial of the present invention, while the amount of the water-soluble polymer contained in the formed hydrogel may suitably be determined according to the type of the water-soluble polymer used, it is, for example, 1-20 wt %, preferably 1-10 wt % and more preferably 1-5 wt % with respect to the total amount of the hydrogel.

Furthermore, in the case of the biomaterial of the present invention, while the amount of the cell contained in the formed hydrogel may suitably be determined according to the type of the cell used, the type and degree of the disease targeted for application and the like, it is, for example, $5.0\times10^6$-$5.0\times10^7$ cells/ml, preferably $8.0\times10^6$-$5.0\times10^7$ cells/ml and more preferably $1.0\times10^7$-$5.0\times10^7$ cells/ml.

In the case of the biomaterial of the present invention, other than the water-soluble polymer, the cell and water, the formed hydrogel may further contain a component for promoting cell proliferation, a pharmaceutically active component, a buffer, a stabilizer and the like, as appropriate.

In order to covalently bind the reactive functional group A incorporated into the water-soluble polymer with the reactive functional group B incorporated into the cell surface to form a hydrogel, they can be incubated under such conditions that allow the reactive functional group A and the reactive functional group B to covalently bind to each other according to their types.

Moreover, the biomaterial of the present invention may be administered in a form of liquid or sol so as to form a hydrogel at an affected site. Specifically, since it is in a form of liquid or sol upon administration, it has fluidity and thus can be administered with a syringe or the like, which is favorable in terms of easy handling. For example, in order to obtain a biomaterial that is in a form of liquid or sol upon administration and that forms a hydrogel after being administered to an affected site, reactive functional groups that can be linked via click chemistry (for example, an alkynyl group or an azide group) can be used as the reactive functional group A and the reactive functional group B. Since an alkynyl group and an azide group undergo a covalent bond once they are placed together, a water-soluble polymer having the reactive functional group A and a cell having the reactive functional group B can be mixed in an aqueous solvent such as water or physiological saline before the biomaterial is administered to an affected site to prepare a mixture in a form of liquid or sol, and then this mixture in a form of liquid or sol can be administered in an appropriate amount to the affected site with a syringe or the like before the covalent bond proceeds to form a hydrogel. The administered mixture in a form of liquid or sol undergoes a covalent bond via click chemistry at the affected site to form a hydrogel.

Furthermore, the biomaterial of the present invention may form a hydrogel in advance before administration so that the hydrogel itself can be administered to the affected site. In order to form a hydrogel in advance before administration, for example, the following methods can be employed: (1) a method in which a water-soluble polymer having a reactive functional group A and a cell having, on the surface thereof, a functional group B that can covalently bind to the reactive functional group A are mixed in an aqueous solvent using a mold having a predetermined shape and incubated under conditions that allow the reactive functional group A and the reactive functional group B to covalently bind to each other, thereby forming a hydrogel having a desired shape; or (2) a method in which a water-soluble polymer having a reactive functional group A and a cell having, on the surface thereof, a functional group B that can covalently bind to the reactive functional group A are mixed in an aqueous solvent and incubated under conditions that allow the reactive functional group A and the reactive functional group B to covalently bind to each other to form a hydrogel, which can thereafter be cut into a predetermined shape.

Moreover, when two or more hydrogels, which are each formed by using a water-soluble polymer having a reactive functional group A and a cell having, on the surface thereof, a functional group B to covalently bind the reactive functional group A with the reactive functional group B, are incubated together while they are making contact with each other, one hydrogel binds to the other on the contact surface by cadherin-mediated cell adhesion, whereby the two or more hydrogels are adhered to each other. Therefore, in a case where a hydrogel is to be formed in advance to administer the hydrogel itself to an affected site, two or more first hydrogels can be formed using a water-soluble polymer having a reactive functional group A and a cell having a reactive functional group B on the surface, and then they can be incubated while making contact with each other to have a predetermined shape, thereby fabricating a second hydrogel comprising the two or more first hydrogels that are adhered to each other. Thus, this second hydrogel can be administered to the affected site. In this case, the two or more first hydrogels can be incubated while they are making contact with each other by immersing the two or more first hydrogels that are making contact with each other in a medium that allows cell growth. Moreover, since the two or more first hydrogels are adhered to each other by intercellular adhesion mediated by cadherin that requires calcium ions, the above-mentioned medium preferably contains 0.2 wt % or more and more preferably 0.2-1.0 wt % of calcium ions. The conditions for incubating the two or more first hydrogels while they are making contact with each other include, for example, a temperature around 37° C. for a period of 6-24 hours.

[Usage]

The biomaterial of the present invention can be administered to an injured or defect site of a biological tissue for repairing said biological tissue. When the biomaterial of the present invention is applied to an injured or defect tissue, the hydrogel fixed to the affected site is gradually hydrolyzed during which the biological tissues is efficiently repaired by the cell maintained in the hydrogel.

Biological tissues targeted for repairing with the biomaterial of the present invention is not particularly limited, and may be epithelial tissue, connective tissue, muscle tissue, neural tissue or any organ formed of a composite thereof. For example, while skin, bone, cartilage, a muscle such as cardiac muscle or the like may be targeted by the present invention, from the viewpoint of enhancing the repairing effect, it is preferably epithelial tissue and/or connective tissue adjacent to epithelial tissue (in particular, skin), muscle tissue (in particular, skeletal muscle) or the like. More preferably, the present invention is effective for third-degree burns, a crush or a defect of a bone or a muscle, or the like.

A method for administering the biomaterial of the present invention may appropriately be determined according to the type of the biological tissues targeted for repairing. For example, it may be transdermal administration, topical administration by injection, or the like.

In addition, the dose of the biomaterial of the present invention can suitably be determined according to the type and the state of the biological tissues targeted for repairing. Since the site administered with a biological tissue repairing agent of the present invention can be regenerated into normal tissue, the biomaterial of the present invention may be administered in such an amount to fill in the region to be regenerated.

EXAMPLES

Hereinafter, the present invention will be described specifically by means of examples, although the following examples should not be construed to limit the present invention.

1. Synthesis of Mannosamine Incorporating Azide Group and Having Hydroxy Group Acetylated D-mannosamine hydrochloride and azidoacetic acid were subjected to coupling reaction using DMT-MM (4-(4,6-dimethoxy-1,3,5-triazine-2-yl)-4-methylmorpholinium chloride) as a condenser. D-mannosamine hydrochloride (200 mg, 0.93 mmol) was weighed and dissolved in 40 mL of ultrapure water (Milli-Q water). To this, DMT-MM (515 mg, 1.86 mmol) and azidoacetic acid (139 µL, 1.86 mmol) were added and heated to 45° C. to allow reaction for 2 days. Two days later, the solvent was removed with an evaporator and purification was roughly carried out with methanol to remove the precipitated by-product and unreacted product. Column purification was carried out by silica gel chromatography and only a solution of a fraction that was confirmed to contain the product of interest by thin-layer chromatography (TLC) was collected. The composition of the eluent used upon this was methanol:chloroform=2:1 (volume ratio). The synthesized product was subjected to IR measurement to confirm whether a compound having a —CO—$CH_2$—$N_3$ group bound to the amino group of D-mannosamine (hereinafter, "ManNAz") was synthesized.

Next, four hydroxy groups of ManNAz were acetylated. ManNAz and the flask used as the reaction container were dried under reduced pressure for a day for dehydration. ManNAz (200 mg, 0.76 mmol) was dissolved in pyridine (5.5 mL, 68.0 mmol) in nitrogen atmosphere, to which acetic anhydride (0.6 mL, 6.84 mmol) was added to allow reaction for 30 minutes. The synthesized product was purified by extraction using a funnel as follows. The product was dissolved in dichloromethane and extracted using a 1 M aqueous hydrochloric acid solution, a saturated aqueous solution of sodium hydrogen carbonate and saturated saline. The organic phase was dehydrated with magnesium sulfate, and the solution was collected by vacuum filtration. The solvent was removed using an evaporator. The synthesized product obtained was subjected to IR measurement, ESI-MS measurement and $^1$H-NMR measurement to confirm that azide-modified mannosamine, in which a —CO—$CH_2$—$N_3$ group was bound to the amino group of D-mannosamine and the four hydroxy groups of D-mannosamine were acetylated (hereinafter, "$Ac_4$ManNAz"), was synthesized.

2. Cytotoxicity Test of $Ac_4$ManNAz

In order to examine the cytotoxicity of the synthesized $Ac_4$ManNAz, mouse myoblasts (C2C12 cells) were used to evaluate toxicity to cells by WST-1 assay. The cells were seeded in a 96-well plate at $1\times10^4$ cells/well, to which a predetermined amount of $Ac_4$ManNAz dissolved in a DMEM medium (final concentrations of 0, 0.0001, 0.001, 0.01, 0.1 and 1 mM) was added to culture the resultant in a $CO_2$ incubator at 37° C. for one day. To each well, 10 µL of a WST-1 solution (WST-1:1-Methoxy PMS=9:1) was added to allow reaction in the $CO_2$ incubator for 2 hours. Thereafter, absorbance was determined with a microplate reader. Cell viability was calculated from the absorbance.

The results from the WST-1 assay are shown in FIG. 1. Since the cell viability were 90% or higher at all concentrations, the synthesized $Ac_4$ManNAz was found to be applicable without having toxicity to cells at least in an amount of 5-100 µM.

4. Preparation of Azide-Modified Cells by Cell Sugar Metabolism Reaction of $Ac_4$ManNAz C2C12 cells were cultured in a DMEM medium containing 100 µM of $Ac_4$ManNAz for 3 days to allow biosynthesis of azide-modified sialic acid at the end of the glycan of the cell membrane protein via cell sugar metabolism reaction of $Ac_4$ManNAz. The cultured cells were washed with PBS twice. To confirm whether an azide group was introduced, carboxyrhodamine 110 DBCO (final concentration 5 µM) was added to the medium and allowed to react in the $CO_2$ incubator for an hour. Subsequently, the cells were washed with PBS twice, to which a live cell imaging buffer (composition of the solution: 140 mM NaCl, 2.5 mM KCl, 1.8 mM $CaCl_2$), 1.0 mM MgCl2 and 20 mM HEPES pH 7.4) was added to observe the cells with a confocal microscope.

Confocal microscope images of the cells after the reaction with carboxyrhodamine 110 DBCO are shown in FIG. 2. While no carboxyrhodamine 110-derived green fluorescence was observed for cells that were not added with $Ac_4$ManNAz, strong green fluorescence was observed only on the surface of the cell membrane for cells added with $Ac_4$ManNAz. These results show that $Ac_4$ManNAz incorporated into the cells was introduced into the glycan of the cell membrane protein via the sugar metabolism pathway, showing that the azide group was capable of click reaction in water. In addition, results from determining the fluorescence intensity on the surface of the cell membrane are shown in FIG. 3. While the green fluorescence intensity increased along with the increase in the $Ac_4$ManNAz concentration, it reached the plateau at 100 µM or more. This shows that a concentration of $Ac_4$ManNAz that allows a maximum amount of azide groups to be introduced into the cell surface was 100 µM. Hereinafter, cells obtained by culturing C2C12 cells in a DMEM medium containing $Ac_4$ManNAz are referred to as "azide-modified C2C12 cells".

5. Analysis of Cell Proliferation Capacity of Azide-Modified Cells

Azide-modified C2C12 cells (N3(+)–C2C12) and non-azide-modified C2C12 cells (untreated C2C12 cells, N3(−)–C2C12) were each seeded in a 6-well plate at $5 \times 10^4$ cells/well and cultured for a week. Meanwhile, the cells were collected to count the cells by Trypan blue assay. From the results, cell growth curves showing correlation between days of culture and total cell number was generated.

The cell growth curves of the azide-modified C2C12 cells and the non-azide-modified C2C12 cells are shown in FIG. 4. These results show that the doubling times of the azide-modified C2C12 cells and the non-azide-modified C2C12 cells were comparable, and thus incorporation of an azide group into a glycan on a cell membrane does not affect cell proliferation.

6. Synthesis of Branched Alginate

The synthesis pathway of branched alginate (bAlg) is shown in FIG. 5. Using DMT-MM as a condenser, bAlg was synthesized through coupling reaction between sodium alginate (Mw: 100,000) and 4-arm PEG-amine (SUNBRIGHT PTE-200PA, Mw: 20,000) as follows. Sodium alginate (100 mg, 1 µmol) was weighed and dissolved in 15 mL of ultrapure water (Milli-Q water). To this, DMT-MM (33.2 µg, 0.12 µmol) and 4-arm PEG-amine (2 mg, 0.1 µmol) were added and the resultant was filled up to a total solution amount of 20 mL. Six hours after the start of the reaction, a dialysis membrane (MWCO: 14,000) was used to perform dialysis for 2 days, which was further followed by 2 days of lyophilization to give a synthesized product. The size of the synthesized product was determined by DLS measurement. In addition, molecular composition was determined by $^1$H-NMR measurement (D20, 85° C.).

The number of binding 4-arm-PEG per 1 alginate molecule was found to be 0.1. This was comparable to the feed amounts of alginate: 4-arm-PEG-NH2=10:1 (mole ratio) upon bAlg synthesis, and thus generation of bAlg of interest was confirmed.

7. Synthesis of Cyclooctyne-Modified Branched Alginate

The synthesis pathway of cyclooctyne-modified branched alginate (bAlg-DBCO) is shown in FIG. 6. DMT-MM was as a condenser to allow coupling reaction between bAlg and DBCO-PEG4-amine. bAlg (100 mg, 1 µmol) was dissolved in 15 mL of ultrapure water (Milli-Q water). To this, DMT-MM (4.2 mg, 15.3 µmol) and DBCO-PEG4-amine (6.7 mg, 12.7 µmol) were added to allow reaction at room temperature for 24 hours while using aluminum foil to shield the light. After 24 hours, a dialysis membrane (MWCO: 14,000) was used to perform dialysis for 2 days, which was further followed by 2 days of lyophilization to give a synthesized product (bAlg-DBCO). The number of DBCO bound per 1 bAlg molecule was calculated by $^1$H-NMR measurement (D20, 85° C.).

The result from the $^1$H-NMR measurement showed that the number of binding DBCOper 1 bAlg molecule in the synthesized bAlg-DBCO was 13. Accordingly, the approximate molecular weight of bAlg-DBCO was found to be 1,026,807 g/mol.

8. Confirmation of click reaction between azide-modified cells and bAlg-DBCO bAlg-DBCO obtained above was labeled with FITC (bAlg-DBCO-FITC). bAlg-DBCO (30 mg, 0.029 µmol) was weighed and dissolved in 5 ml of ultrapure water (Milli-Q water). To this, DMT-MM (2.9 mg, 10.5 µmol) and FITC (1.2 mg, 2.9 µmol) were added and the resultant was filled up to a total solution amount of 6 mL. Two days after the start of the reaction, a dialysis membrane (MWCO: 14,000) was used to perform dialysis for 2 days, which was further followed by 2 days of lyophilization to give a synthesized product (bAlg-DBCO-FITC).

An aqueous solution of bAlg-DBCO-FITC (0.5 mg/mL) was prepared and the pH was adjusted to 7.4 with an aqueous KOH solution. C2C12 cells were cultured in a DMEM medium with 100 µM of $Ac_4ManNAz$ for 3 days for azide-modification. The azide-modified cells were peeled off from the dish by a trypsin treatment, and subjected to centrifugation (1000 rpm, 3 min) to prepare pellets of the cell. The supernatant containing $Ac_4ManNAz$ that was not incorporated into the azide-modified cells was removed with an aspirator. Then, a DMEM medium was added to prepare a cell suspension again, which was left to stand still in a $CO_2$ incubator for an hour. An hour later, pellets of $4.5 \times 10^4$ azide-modified cells were prepared, to which 125 µL of an aqueous 2% bAlg-DBCO-FITC solution and 375 µL of a DMEM medium were added to give final bAlg-DBCO-FITC concentration of 0.5%. The resultant was allowed to react in a shaking incubator for 30 minutes. Thereafter, the azide-modified cells were washed in 1 mL of PBS solution twice, and placed in a 8-well chamber to observe the azide-modified cells with a confocal microscope. Additionally, the same procedure was conducted using FITC-labeled bAlg (bAlg-FITC) instead of bAlg-DBCO-FITC.

Confocal microscope images of the azide-modified C2C12 cells that were reacted with bAlg-DBCO-FITC and the azide-modified C2C12 cells that were reacted with bAlg-FITC are shown in FIG. 7. With bAlg-DBCO-FITC, FITC-derived green fluorescence was observed on the cell membrane of the azide-modified C2C12 cells. Since no green fluorescence was observed with the combination of the azide-modified cells and bAlg-FITC, the azide group incorporated into the glycan of the cell membrane protein was found to undergo click reaction with the alkynyl group of bAlg-DBCO.

9. Fabrication of Hydrogel

C2C12 cells were cultured in a DMEM medium with 100 µM of $Ac_4ManNAz$ for 3 days for azide-modification. The azide-modified cells were peeled off from the dish by a trypsin treatment, and subjected to centrifugation (1000 rpm, 3 min) to prepare pellets of the azide-modified cells. The supernatant containing $Ac_4ManNAz$ that was not incorporated into the cells was removed with an aspirator. Then, a DMEM medium was added to prepare a cell suspension again, which was left to stand still in a $CO_2$ incubator for an hour to nurse the azide-modified cells. An hour later, pellets of a predetermined number of azide-modified cells ($0.5 \times 10^6$, $1 \times 10^6$, $2 \times 10^6$) were prepared in Eppendorf tubes, to which an aqueous bAlg-DBCO solution obtained by dissolving bAlg-DBCO obtained above in a HEPES buffer (200 mM HEPES; where pH was adjusted to 7.4 with 800 mM of an aqueous KOH solution) (where bAlg-DBCO concentration was adjusted to 1 wt % or 2 wt % and pH was adjusted to 7.4 with an aqueous KOH solution) was added, and the resultant was homogeneously suspended by gently pipetting for 30 times. The suspension was transferred to a sample tube to examine whether or not gelation took place after a predetermined period of time (after 0, 0.5, 3, 6 and 24 hours) by a test tube inverting method (a method in which a test tube is tilted and maintained there for 30 seconds to evaluate if the solution flows or does not flow to determine whether it is a sol or a gel, respectively). Additionally, the same procedure was conducted using bAlg instead of bAlg-DBCO.

The results from the test tube inverting method are shown in FIG. 8. At a high bAlg-DBCO concentration (2%), gel was formed with any cell numbers ($0.5 \times 10^6$, $1 \times 10^6$, $2 \times 10^6$).

Gelation did not occur with the combination of the azide-modified cells and bAlg, i.e., the control. Accordingly, the gel was found to be obtained via the click cross-linking reaction between the azide-modified C2C12 cells and bAlg-DBCO. In addition, with the combination of $2 \times 10^6$ azide-modified cells and a 2% bAlg-DBCO solution, gelation occurred by 30 seconds after the reaction. Furthermore, a gel formed under these conditions did not collapse even when 500 µL of a DMEM medium was added onto the gel and the resultant was left to stand still in a $CO_2$ incubator for an hour. FIG. 9 shows a picture of the gel that was placed on a glass slide after removing the medium. The gel did not collapse and maintained its shape on the glass slide. Accordingly, a hydrogel formed using bAlg-DBCO and azide-modified cells was found to have relatively good handling property.

10. Fabrication of Hydrogels Using Various Cells

Cell types other than C2C12 cells, namely, MCF-7 cells (human breast cancer cells) and HL-60 cells (human leukemia cells), were also used to fabricate hydrogels. The hydrogels were fabricated as described above. The cells were cultured in a DMEM medium (MCF-7 cells) or a RPMI medium (HL-60 cells) containing 100 µM of $Ac_4ManNAz$, respectively, for 3 days for azide modification. Pellets of $2 \times 10^6$ azide-modified cells were suspended in an aqueous 2 wt % bAlg-DBCO solution (pH was adjusted to 7.4 with an aqueous KOH solution) to examine the presence of gelation by a test tube inverting method.

The results of click cross-linking reactions using azide-modified MCF-7 cells and azide-modified HL-60 cells are shown in FIG. 10. The MCF-7 cells and the HL-60 cells both formed hydrogels after 30 seconds of agitation under conditions of a cell number of $2 \times 10^6$ and a bAlg-DBCO concentration of 2 wt %. Specifically, since cells were azide-modified by a universal protocol in this procedure, not only the three types of cells used in this example but also wide types of cells having tissue-regenerating capacity were confirmed to be capable of fabricating a hydrogel.

11. Fabrication of Hydrogel Using Cryopreserved Cells

C2C12 cells were cultured in a DMEM medium with 100 µM of $Ac_4ManNAz$ for 3 days, and the prepared azide-modified C2C12 cells were cryopreserved. The cryopreserved azide-modified C2C12 cells were thawed and cultured again to prepare pellets of $2 \times 10^6$ azide-modified cells in an Eppendorf tube. To this, 100 µL of an aqueous 2% bAlg-DBCO solution dissolved in a HEPES buffer (where pH was adjusted to 7.4 with an aqueous KOH solution) was added to allow reaction to examine the presence of gelation by a test tube inverting method.

FIG. 11 shows a picture of the hydrogel fabricated using the cryopreserved azide-modified cells. As a result, gel was formed within a minute after using and mixing the cryopreserved azide-modified cells with the bAlg-DBCO solution. This shows that the azide-modified cells can be preserved for a long time by cryopreservation and has sufficiently long shelf-life as a chemical material.

12. Evaluation of Molding Properties of Hydrogel

C2C12 cells were cultured in a DMEM medium with 100 µM of $Ac_4ManNAz$ for 3 days to prepare azide-modified C2C12 cells. Subsequently, pellets of $2 \times 10^6$ azide-modified C2C12 cells were prepared, to which 100 µL of an aqueous 2 wt % bAlg-DBCO-FITC solution dissolved in a HEPES buffer (where pH was adjusted to 7.4 with an aqueous KOH solution) was added. The resultant was homogeneously suspended by gently pipetting for 30 times. The suspension was discharged to write the word "FIRST" on a glass slide using a pipette, which was left to stand still in a $CO_2$ incubator at 37° C. for 30 minutes.

As can be appreciated from FIG. 12, the gel can be formed into an intended shape. Since the cell-hybrid gel can be used to write words freely, it was found to have a high molding property.

13. Confocal Microscope Observation and SEM Observation of Hydrogel

C2C12 cells were cultured in a DMEM medium with 100 µM of $Ac_4ManNAz$ for 3 days, and the prepared azide-modified C2C12 cells were stained with CytoTell™ Red. Pellets of $2 \times 10^6$ azide-modified C2C12 cells were prepared, and the resultant was mixed with 100 µL of an aqueous bAlg-DBCO-FITC solution that was obtained by dissolving bAlg-DBCO-FITC prepared above in a HEPES buffer to 2 wt %, to prepare cell cross-linked hydrogel in a sample tube. Subsequently, 500 µL of a DMEM medium was gently added and the resultant was left to stand still in a $CO_2$ incubator for an hour. Thereafter, a spatula was used to take out the gel on a 3.5-cm glass bottom dish. The obtained gel was observed with a confocal microscope. After observation, the gel was washed twice with 1 mL of a PBS solution and lyophilized. The resulting sample was fractured and fixed on a sample stage such that the fractured surface was facing upward. The sample was coated with osmium and the gel network structure was observed with a scanning electron microscope (JSM-7001FA, JEOL Ltd., hereinafter SEM).

FIG. 13 shows a three-dimensional image of the fabricated hydrogel observed with the confocal microscope. bAlg-DBCO-FITC-derived green fluorescence can be seen over the entire three-dimensional image, in which cells stained in red with CytoTell™ Red can be seen. Specifically, the resulting hydrogel was found to be a three-dimensional structure in which the cells are uniformly dispersed across the whole system. FIG. 14 shows a partially enlarged view inside the hydrogel. While the cells are surrounded by a fibrous alginate network, the alginate network does not exist where the cells are. Specifically, the cells and the alginate network were found to have a micro-phase separated structure in the gel. FIG. 15 shows a SEM image of the fractured surface obtained after lyophilizing the obtained hydrogel. As a result, a sponge-like network structure typical of a gel was observed, where the gel network and the cells were confirmed to be linking to each other.

14. Evaluation of Cell Viability in Hydrogel

C2C12 cells were cultured in a DMEM medium with 100 µM of $Ac_4ManNAz$ for 3 days to prepare azide-modified C2C12 cells. The azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated was removed with an aspirator. A DMEM medium was further added to the pellets of the azide-modified C2C12 cells to prepare a cell suspension again, which was left to stand still in a $CO_2$ incubator for an hour to nurse the azide-modified C2C12 cells. An hour later, pellets of a predetermined number of the azide-modified C2C12 cells were prepared in an Eppendorf tube, to which an aqueous bAlg-DBCO solution obtained by dissolving bAlg-DBCO prepared above to 2 wt % (where pH was adjusted to 7.4 with an aqueous KOH solution) was added and the resultant was agitated by gently pipetting for 30 times. 30 µL/well of the resulting suspension was dispensed into a 8-well chamber. After the resultant was left to stand still in a $CO_2$ incubator for 30 minutes, 400 µL each of a DMEM medium was added for culture. After a predetermined days of culture (Days 0, 1, 3, 5 and 7), 1 µL each of Calcein AM and PI solutions were added to allow staining for 30 minutes. After 30 minutes, the cells in the gel was observed with a confocal microscope. The numbers of the live and dead cells were counted from the three images acquired with the confocal microscope to calculate the cell viability.

FIG. 16 shows confocal microscope images of the azide-modified C2C12 cells in the hydrogel. Cells emitting Calcein AM-derived green fluorescence are live cells while cells emitting PI-derived red fluorescence are dead cells. On Day 0 immediately after fabricating the hydrogel, a large number of live cells were seen over the gel, which remained the same for a week after culturing the gel. FIG. 17 shows the results obtained by counting the numbers of live and dead cells from the confocal microscope image and calculating the cell viability. The cells in the cell-hybrid gel maintained a cell viability of 90% or higher even after a week of culture, showing high cell viability. Accordingly, the cells in the hydrogel were confirmed to survive for a long period of time.

15. Evaluation of Proliferation Property of Cells in Hydrogel and Degradation Property of Hydrogel C2C12 cells were cultured in a DMEM medium with 100 μM of $Ac_4ManNAz$ for 3 days to prepare azide-modified C2C12 cells. Then, the azide-modified C2C12 cells were peeled off from the dish by a trypsin treatment, and subjected to centrifugation (1000 rpm, 3 min) to prepare pellets of the azide-modified C2C12 cells. The supernatant containing $Ac_4ManNAz$ that was not incorporated into the azide-modified cells was removed with an aspirator. A DMEM medium was further added to the resulting pellets of the azide-modified C2C12 cells to prepare a cell suspension again, which was left to stand still in a $CO_2$ incubator for an hour to nurse the azide-modified C2C12 cells. An hour later, pellets of a predetermined number of azide-modified C2C12 cells were prepared in an Eppendorf tube, to which 100 μM of an aqueous bAlg-DBCO solution obtained by dissolving bAlg-DBCO prepared above in a HEPES buffer to 2 wt % (where pH was adjusted to 7.4 with an aqueous KOH solution) was added and the resultant was agitated by gently pipetting for 30 times. 10 μL/well of the resulting suspension was dispensed into a 96-well plate, to which 190 μL of a DMEM medium was added to culture in a $CO_2$ incubator. After predetermined days (Days 0, 1, 2, 3, 4, 5, 6 and 7), 5 μL of a WST-1 solution was added to allow reaction for 2 hours. The gel was shredded by pipetting for 50 times, and the resultant was subjected to centrifugation (4000 rpm, 3 min) to allow the cells and the polymer to precipitate. 100 μL of the supernatant was transferred to another 96-well plate to determine the absorbance with a microplate reader. As the control, $1.6 \times 10^3$ C2C12 cells were seeded and cultured in a 24-well plate for a week to see absorbance acquired on each day.

Meanwhile, C2C12 cells were cultured in a DMEM medium with 100 μM of $Ac_4ManNAz$ for 3 days to prepare azide-modified C2C12 cells. Subsequently, azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated into the azide-modified cells was removed with an aspirator. A DMEM medium was further added to the resulting pellets of the azide-modified C2C12 cells to prepare a cell suspension again, which was left to stand still in a $CO_2$ incubator for an hour to nurse the azide-modified C2C12 cells. An hour later, pellets of $1 \times 10^6$ azide-modified C2C12 cells were prepared in an Eppendorf tube, to which 50 μL of an aqueous bAlg-DBCO solution obtained by dissolving bAlg-DBCO prepared above in a HEPES buffer to 2 wt % (where pH was adjusted to 7.4 with an aqueous KOH solution) was added and the resultant was agitated by gently pipetting for 30 times. Subsequently, the suspension was weighed and transferred to an Eppendorf tube, to which 1 mL of a DMEM medium was added. The lid of the Eppendorf tube was loosely closed to make a gap that allowed only $CO_2$ to enter. After predetermined days (Days 0, 1, 2, 3, 4, 5, 6 and 7), the DMEM medium was removed with an aspirator and the gel was weighed. Then, the gel was lyophilized and weighed.

The change in the number of the azide-modified C2C12 cells present in the hydrogel with time is shown in FIG. 18. The number of the azide-modified C2C12 cells in the hydrogel increased until Day 4 and decreased thereafter. The change in the dry weight of the hydrogel with time is shown in FIG. 19. The dry weight of the whole hydrogel was examined, which increased until Day 4 and decreased thereafter. Since the increment of the dry weight of the hydrogel matched well with the dry weight of the increase in the number of cells in the gel, the change in the dry weight seemed primarily caused by the change in the number of the azide-modified C2C12 cells in the hydrogel. FIG. 20 shows an assumed mechanism of degradation of the hydrogel. In the hydrogel of the present invention, the cells serve as cross-linking points, to which the polymer network is linked. Therefore, cell division means a decrease in the number of the cross-linking points. Presumably, the number of the cross-linking points gradually decreased as the gel weight increased with the cell proliferation associated with cell division, whereby the network was no longer maintained and thus the gel collapsed after Day 4. In other words, in the hydrogel of the present invention, proliferation (division) of the cells serving as cross-linking points presumably extended across the entire gel and led to collapse of the gel. Since various cells can be employed to produce a cross-linked gel of this system, the time that takes for gel to collapse is considered to vary depending on the doubling time of the cells used.

16. Evaluation of Adhesion of Cells Present on Surface of Hydrogel

C2C12 cells were cultured in a DMEM medium with 100 μM of $Ac_4ManNAz$ for 3 days to prepare azide-modified C2C12 cells. The azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated into the azide-modified C1C12 cells was removed with an aspirator. A DMEM medium was further added to the pellets of the azide-modified C2C12 cells to prepare a cell suspension again, which was left to stand still in a $CO_2$ incubator for an hour to nurse the azide-modified C2C12 cells. CytoTell™ Red (1 μL/mL) was added for the last 30 minutes to stain the cells. An hour later, pellets of the azide-modified cells were prepared in an Eppendorf tube, to which 100 μL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. Subsequently, a blue pipette tip was modified to make a barrier on a 2-methacryloyloxyethyl phosphorylcholine (MPC) polymer-coated dish and a collagen-coated dish, into which the suspension obtained above was poured to form a gel. 8 mL of a DMEM medium was further added, and the resultant was cultured in a $CO_2$ incubator to examine whether or not the cells present on the surface of the gel adhered to the dish 24 hours later by observing with a confocal microscope.

1 mL of a trypsin solution was added to the hydrogel that adhered to the collagen-coated dish, which was left to stand still in the $CO_2$ incubator for 10 minutes and then transferred to another collagen-coated dish to examine if the gel adhered to the dish again.

Images acquired by phase contrast microscopy and pictures of the gels are shown in FIG. 21. When the hydrogel was placed on a collagen-coated dish, the cells on the surface of the hydrogel adhered to the dish, by which the hydrogel as a whole also adhered to the dish. On the other hand, the cells on the surface of the hydrogel and the hydrogel as a whole did not adhere to the MPC polymer-coated dish. When the hydrogel that adhered to the collagen-coated dish was treated with trypsin, the surface of the hydrogel and the gel as a whole came off from the dish. Then, when the hydrogel was placed on the dish, the gel adhered to the dish again. This means that the scaffold-selective adhesion property of the cells on the surface of the hydrogel extended across the entire hydrogel via the polymer network and thus the hydrogel as a whole showed scaffold-selective adhesion. These results demonstrate that the hydrogel of the present invention is a system that can utilize reaction of cells serving as cross-linking points to provide a novel function to the hydrogel as a whole.

In general, since a large amount of water contained in a hydrogel acts as a lubricant and therefore the coefficient of friction is significantly lower than those of solid materials, a hydrogel is known to be incapable of adhering to most materials. On the other hand, cells are known to adhere to materials with a wide range of surface characteristics. This similarly applies to the case of the hydrogel of the present invention, where the alginate gel does not adhere to a dish but the cells and thus the hydrogel as a whole adheres to the dish. Specifically, the hydrogel of the present invention can solve the major problem of "non-adhesiveness to materials" that have considerably limited the application of gels, and thus is expected to bring about a scientific breakthrough for the gel science.

17. Evaluation of Adhesion Between Hydrogels

C2C12 cells were cultured in a DMEM medium with 100 µM of $Ac_4ManNAz$ for 3 days to prepare azide-modified C2C12 cells. The azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated into the azide-modified C2C12 cells was removed with an aspirator. Subsequently, $2 \times 10^6$ azide-modified C2C12 cells were collected and pelletized in an Eppendorf tube, to which 100 µL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. The resulting suspension was immediately placed into a Transwell and left to stand still in an incubator for 30 minutes. Then, the Transwell was placed directly into a DMEM medium containing 0.5 wt % calcium chloride, which was left to stand still in the incubator for 3 hours to allow formation of a hydrogel in the Transwell. Subsequently, the hydrogel in the Transwell was taken out and overlaid on a hydrogel that was separately fabricated under the same conditions in a Transwell, on which a piece of glass was placed as a weight and left to stand still in a DMEM medium containing 0.5 wt % calcium chloride in the incubator for another 18 hours and then taken out.

The results are shown in FIG. 22. When the hydrogels were overlaid on one another and left to stand still, the cell gels adhered to each other at the interface which did not separate even when they were shaken in the medium or picked up with tweezers.

18. Elucidating Reason for Adhesion Between Hydrogels

C2C12 cells were cultured in a DMEM medium with 100 µM of $Ac_4ManNAz$ for 3 days to prepare azide-modified C2C12 cells. The azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated into the azide-modified C2C12 cells was removed with an aspirator. Subsequently, $2 \times 10^6$ azide-modified C2C12 cells were collected and pelletized in an Eppendorf tube, to which 100 µL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. The resulting suspension was immediately placed into a Transwell and left to stand still in an incubator for 30 minutes. Then, the Transwell was placed directly into a DMEM medium containing 0.5 wt % calcium chloride, which was left to stand still in the incubator for 3 hours to allow formation of a hydrogel in the Transwell. Subsequently, the resulting hydrogel was placed in a 8-well chamber, to which alkyne-modified rhodamine (final concentration 30 µM) was added and the resultant was incubated for an hour to allow reaction of the unreacted azide group present on the surface of the hydrogel. Thereafter, the resultant was washed with PBS. Two hydrogels that were treated in the same manner were overlaid on one another, placed with a weight and left in a DMEM medium ($Ca^{2+}$ ion concentration 0.5%) for 18 hours.

FIG. 23 shows the result obtained by allowing the fabricated hydrogels to react with alkyne-modified rhodamine and observing the resultant with a confocal microscope. Since rhodamine-derived fluorescence was observed on the surface of the cell membrane inside the hydrogel, the presence of unreacted azide group that did not undergo click reaction was revealed. Moreover, FIG. 24 shows the result obtained by overlaying two hydrogels that were reacted with alkyne-modified rhodamine and incubating the two hydrogels. The two hydrogels adhered to each other and thus adhesion between hydrogels was considered to result not from click reaction but from cooperative mechanism of cell attachment or enhancement of entanglement between the gel of the alginate network.

17. Elucidation of Influence of Calcium Ions on Adhesion Between Hydrogels

C2C12 cells were cultured in a DMEM medium with 100 µM of $Ac_4ManNAz$ for 3 days to prepare azide-modified C2C12 cells. The azide-modified C2C12 cells were peeled off from the dish by a trypsin treatment and subjected to centrifugation (1000 rpm, 3 min) to prepare pellets of the azide-modified C2C12 cells. The supernatant containing $Ac_4ManNAz$ that was not incorporated into the azide-modified C2C12 cells was removed with an aspirator. Subsequently, $2 \times 10^6$ azide-modified C2C12 cells were collected and pelletized in an Eppendorf tube, to which 100 µL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. The resulting suspension was placed directly into a Transwell and left to stand still in an incubator for 30 minutes. Then, the Transwell was placed directly into a DMEM medium containing 0.5 wt % calcium chloride, which was left to stand still in the incubator for 3 hours to allow formation of a hydrogel in the Transwell. Subsequently, the hydrogel in the Transwell was taken out and overlaid on a hydrogel that was separately fabricated under the same conditions in a Transwell, on which a piece of glass was placed as a weight and left to stand still in a DMEM medium containing calcium ions (0.2 wt %, 0.3 wt %, 0.4 wt % and 0.5 wt %) in the incubator for another 18 hours and then taken out.

The results are shown in FIG. 25. While adhesion was observed between the hydrogels when the two hydrogels were incubated while they were making contact with each other under the conditions of calcium ions of 0.4 wt % and 0.5 wt %, but adhesion between the hydrogels was not observed when they were incubated under the conditions of calcium ions of 0.3 wt % or lower. Accordingly, concentration of calcium ions was found to be relating to adhesion between the hydrogels. Since cell attachment using cadherin requires calcium ions, adhesion between hydrogels according to the present invention is considered to result from cadherin-mediated cell attachment.

17. Fabrication of Hydrogel Using Biological Tissue 6 mg of $Ac_4ManNAz$ was dissolved in a mixed solvent of DMSO and PBS solution (58% DMSO) to prepare a $Ac_4ManNAz$ solution. 200 μL of the resulting $Ac_4ManNAz$ solution was intraperitoneally administered to a mouse (ICR, 5 weeks old, female) once a day for seven consecutive days for azide-modification of the mouse tissues. A week later, lung, cardiac muscle, skeletal muscle and kidney of the mouse were resected. The resected tissues were allowed to react with 100 μM of carboxyrhodamine 110 DBCO for an hour, then added with a PBS solution, vortexed and left to stand still for 10 minutes. This operation was repeated for 3 times. As control, tissues resected from a mouse that was not administered with the $Ac_4ManNAz$ solution were allowed to react with carboxyrhodamine 110 DBCO for an hour. Furthermore, the tissues of the mouse administered with the $Ac_4ManNAz$ solution were allowed to react with an aqueous bAlg-DBCO solution obtained by dissolving bAlg-DBCO obtained above in a HEPES buffer to 0.1 wt % (where pH was adjusted to 7.4 with an aqueous KOH solution) to examine whether or not click reaction occurs between the azide-modified cells forming the tissues and bAlg-DBCO by observing with a confocal microscope. In order to carry out gelation reaction using mouse tissues, the $Ac_4ManNAz$ solution was administered to a mouse in the same manner as described above and lung, brain, muscle tissue, kidney, heart and liver were resected from the mouse. An aqueous bAlg-DBCO solution obtained by dissolving bAlg-DBCO in a HEPES buffer to 2 wt % was added to the resected tissue to give the same weight as the resected tissue and pipetted to examine the presence of gelation by test tube inverting method.

FIG. 26 shows images obtained by allowing tissues resected from an untreated mouse (lung, cardiac muscle, skeletal muscle and kidney) and the tissues resected from the mouse administered with the $Ac_4ManNAz$ solution to react with bAlg-DBCO-FITC to observe with a confocal microscope. While FITC-derived green fluorescence was observed in all of the tissues from the mouse administered with the $Ac_4ManNAz$ solution, green fluorescence was not observed with the control mouse that was not administered with the $Ac_4ManNAz$ solution. Accordingly, it was found that administration of $Ac_4ManNAz$ can enable azide-modification in a living body and the azide group at the cell surface forming the tissue was also capable of click reaction with a cyclooctyne group. With these findings, an aqueous 2 wt % bAlg-DBCO solution and each of the azide-modified tissues were tested for gel reaction. The presence of gelation was examined by a test tube inverting method and the results are shown in FIG. 27. From these results, formation of a hydrogel was confirmed in all of the tissues. Accordingly, we were able to fabricate a tissue hybrid gel in which a tissue is cross-linked with a polymer for the first time in the world.

18. In Vivo Fabrication of Hydrogel

C2C12 cells transfected with LifeAct-EGFP gene were prepared. The C2C12 cells were cultured in a DMEM medium with 100 μM of $Ac_4ManNAz$ for 3 days to prepare azide-modified C2C12 cells. Subsequently, pellets of $4 \times 10^6$ azide-modified C2C12 cells were prepared, to which 200 μL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. 200 μL of the resulting suspension was subcutaneously injected into the back of a nude mouse (BALB/c-nu/nu, 5 weeks old, female). Thirty minutes after the injection, the injected site was incised to examine whether the injected suspension formed a hydrogel.

A picture of the abdominal cavity of the mouse is shown in FIG. 28. Since a hydrogel was found at the injected site, the suspension of the azide-modified cells and bAlg-DBCO was found to be injectable into a living body and was found to be capable of forming a hydrogel in the injected living body.

19. Test of Administering Hydrogel into Injured Femoral Muscle of Mouse Model

Nude mice (females, 5 weeks old, BALB/c-nu/nu) were grouped into a hydrogel administration group and a PBS administration group (3 mice in each group). About 100 mg of the inner femoral muscle of one limb of each nude mouse was resected to make an injury and then the skin was sutured with nylon thread. One day after making the injury, the nude mice in the respective groups were treated as follows.

The hydrogel administration group was treated as follows. C2C12 cells transfected with LifeAct-EGFP gene were cultured in a DMEM medium with 100 μM of $Ac_4ManNAz$ for 3 days to prepare azide-modified C2C12 cells. Pellets of $5 \times 10^6$ azide-modified C2C12 cells were prepared, to which 250 μL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. 250 μL of the resulting suspension was subcutaneously injected into the injured muscle site a day after making the injury.

Meanwhile, for the PBS administration group, $5 \times 10^6$ C2C12 cells transfected with LifeAct-EGFP gene was suspended in 250 μL of PBS and this suspension was injected into the injured muscle site a day after making the injury.

The muscle strength of the injured limb was measured with time from a day before to 15 days after the day of injury. The muscle strength of the limb was measured with a small animal grip-strength meter ("GPM-100B", Melquest Ltd.) after covering the fingers of the uninjured limb with masking tape for restraint. Assuming that the muscle strength upon making the injury was 0, the muscle strength on days following the day of injury was measured and the recovery rate was determined from their difference. In addition, the injured site was incised to observe the state of the inner femoral muscle on Day 15 after the injury.

A fluorescence microscope image of the incised site of the hydrogel administration group is shown in FIG. 29. In the hydrogel administration group, the transplanted cells were found to be dense and highly oriented. In addition, generation of muscle fibers, although immature, was observed in the hydrogel administration group. An analysis of H&E stained tissue section also gave similar results, where muscle fibers existed at a high proportion in the reconstructed tissue of the hydrogel administration group. Changes in the muscle strength with time is shown in FIG. 30. Assuming that the muscle strength after resection was 0, the recovery rate from that point was measured. The recovery of the muscle strength was significantly higher for the hydrogel administration group than the PBS administration group. Since the hydrogel of the present invention can retain cells in the vicinity of the injured site, formation of muscle fibers by cell fusion was promoted, which seemed to have led to high muscle strength recovery.

20. Test of Administering Hydrogel into Injured Femoral Muscle of Mouse Model (2)

Nude mice (females, 5 weeks old, BALB/c-nu/nu) were grouped into a hydrogel administration group and a PBS administration group (3 mice in each group). About 100 mg of the inner femoral muscle of one limb of each nude mouse was resected to make an injury and then the skin was sutured with nylon thread. One day after making the injury, the nude mice in respective groups were treated as follows.

The hydrogel administration group was treated as follows. Human adipose-derived stem cells (ADSC) having cell membrane labeled with DiI were cultured in a DMEM medium with 100 µM of $Ac_4ManNAz$ for 3 days to prepare azide-modified ADSC. Pellets of $4.5 \times 10^6$ azide-modified ADSC were prepared, to which 200 µL of an aqueous bAlg-DBCO solution obtained by dissolving bAlg-DBCO prepared above in a HEPES buffer to 2 wt % (where pH was adjusted to 7.4 with an aqueous KOH solution) was added and agitated by gently pipetting for 30 times. 200 µL of the resulting suspension was injected into the injured muscle site a day after making the injury.

Meanwhile, for the PBS administration group, $5 \times 10^6$ ADSC having cell membrane labeled with DiI were suspended in 250 µL of PBS and this suspension was injected into the injured muscle site a day after making the injury.

The muscle strength of the injured limb was measured with time from a day before to 14 days after the day of injury. The muscle strength of the limb was measured with a small animal grip-strength meter ("GPM-100B", Melquest Ltd.) after covering the fingers of the uninjured limb with masking tape for restraint. The muscle strength on days following the day of injury was measured and the recovery rate was determined (provided that the muscle strength before the injury was 100%). In addition, the injured site was incised to observe the state of the inner femoral muscle on Day 14 after the injury.

Fluorescence microscope images of the incised sites are shown in FIG. 31. Although regeneration of the muscle tissue was not observed for the PBS administration group, regeneration of the muscle fibers was confirmed for the hydrogel administration group, and thus the present invention was found to be more effective in promoting regeneration of the muscle tissue than conventional methods. In addition, changes in the muscle strength with time is shown in FIG. 32. The recovery of the muscle strength was significantly higher for the hydrogel administration group than the PBS administration group.

The invention claimed is:

1. A method for repairing a biological tissue, comprising:
applying to an affected site a biomaterial comprising
a water-soluble polymer having a reactive functional groups A; and
mesenchymal stem cells having tissue-regenerating capacity and having, on the surface of the cells, reactive functional groups B that can covalently bind to the reactive functional groups A,
wherein the biomaterial presents a hydrogel state when the reactive functional groups A covalently bind to the reactive functional groups B,
wherein the water-soluble polymer is a polysaccharide thickener, and
wherein the mesenchymal cells having tissue-regenerating capacity serve as cross-linking points of the hydrogel for chemically binding with the water-soluble polymer, wherein the affected site to which the biomaterial is applied is selected from the group consisting of (i) epithelial tissue, (ii) connective tissue adjacent to epithelial tissue, and (iii) skeletal muscle tissue.

2. A method for repairing a biological tissue, comprising:
applying to an affected site a biomaterial in a form of a liquid or sol, wherein said biomaterial forms a hydrogel after application to said affected site, said biomaterial comprising
a water-soluble polymer having a reactive functional groups A; and
mesenchymal stem cells having tissue-regenerating capacity and having, on the surface of the cells, reactive functional groups B that can covalently bind to the reactive functional groups A,
wherein the biomaterial presents a hydrogel state when the reactive functional groups A covalently bind to the reactive functional groups B,
wherein the water-soluble polymer is a polysaccharide thickener,
wherein the mesenchymal cells having tissue-regenerating capacity serve as cross-linking points of the hydrogel for chemically binding with the water-soluble polymer,
wherein said affected site to which the biomaterial is applied is selected from the group consisting of (i) epithelial tissue, (ii) connective tissue adjacent to epithelial tissue, and (iii) skeletal muscle tissue.

3. The method of claim 2, wherein the reactive functional group A is an alkynyl group and the reactive functional group B is an azide group.

4. The method of claim 2, wherein the polysaccharide thickener is alginate.

5. The method of claim 2, wherein the water-soluble polymer is branched because two or more linear water-soluble polymers are bound to a branched compound.

6. The method of claim 3, wherein the reactive functional group A covalently binds to the reactive functional group B at said affected site inside the biological tissue, is an injured biological tissue, and wherein said cells remain in the hydrogel at the affected site, allowing for effective repairing of the injured biological tissues and thus the biomaterial presents a hydrogel state after administration.

7. The method of claim 2, wherein said cells in said biomaterial can regenerate into normal tissue.

8. The method of claim 2, which is applied to an injured or defect muscle tissue.

9. The method of claim 7, wherein said cells are human cells.

10. The method of claim 9, wherein said human cells are human adipose-derived stem cells.

11. The method of claim 2, wherein the number of reactive functional groups A incorporated into the water-soluble polymer is 2-60 per molecule of the water-soluble polymer.

12. The method of claim 2, wherein the number of reactive functional groups A incorporated into the water-soluble polymer is 5-50 per molecule of the water-soluble polymer.

13. The method of claim 2, wherein the number of reactive functional groups A incorporated into the water-soluble polymer is 5-30 per molecule of the water-soluble polymer.

14. The method of claim 11, wherein the amount of water-soluble polymer contained in the hydrogel is 1-20 wt %, with respect to the total amount of the hydrogel or the amount of cells contained in the hydrogel is $5.0 \times 10^6 - 5.0 \times 10^7$ cells/ml.

15. The method of claim 12, wherein the amount of water-soluble polymer contained in the hydrogel is 1-10 wt %, with respect to the total amount of the hydrogel or the amount of cells contained in the hydrogel is $8.0 \times 10^6 - 5.0 \times 10^7$ cells/ml.

16. The method of claim 13, wherein the amount of water-soluble polymer contained in the hydrogel is 1-5 wt %, with respect to the total amount of the hydrogel or the amount of cells contained in the hydrogel is $1.0 \times 10^7 - 5.0 \times 10^7$ cells/ml.

* * * * *